(12) United States Patent
Flanagan et al.

(10) Patent No.: US 7,955,382 B2
(45) Date of Patent: Jun. 7, 2011

(54) ENDOPROSTHESIS WITH ADJUSTABLE SURFACE FEATURES

(75) Inventors: Aiden Flanagan, Galway (IE); Dave McMorrow, Galway (IE); Anthony Malone, Galway (IE); Tim O'Connor, Galway (IE); Barry Heaney, Galway (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 69 days.

(21) Appl. No.: 11/855,541

(22) Filed: Sep. 14, 2007

(65) Prior Publication Data

US 2008/0071351 A1    Mar. 20, 2008

Related U.S. Application Data

(60) Provisional application No. 60/845,047, filed on Sep. 15, 2006.

(51) Int. Cl.
*A61F 2/06* (2006.01)
(52) U.S. Cl. ...................................... 623/1.42
(58) Field of Classification Search ............... 623/1.13, 623/1.15, 1.23, 1.34, 1.38–1.54, 23.7, 23.71, 623/23.72, 23.73, 23.74, 23.75, 23.76
See application file for complete search history.

(56) References Cited

U.S. PATENT DOCUMENTS

| | | | |
|---|---|---|---|
| 3,687,135 A | 8/1972 | Stroganov et al. | |
| 4,539,061 A | 9/1985 | Sagiv | |
| 4,634,502 A | 1/1987 | Callahan et al. | |
| 5,059,211 A | 10/1991 | Stack et al. | |
| 5,079,203 A | 1/1992 | Pinnavaia | |
| 5,091,205 A | 2/1992 | Fan | |
| 5,195,969 A | 3/1993 | Wang et al. | |
| 5,236,447 A * | 8/1993 | Kubo et al. | 623/1.13 |
| 5,270,086 A | 12/1993 | Hamlin | |
| 5,292,558 A | 3/1994 | Heller et al. | |
| 5,304,195 A | 4/1994 | Twyford, Jr. et al. | |
| 5,366,504 A | 11/1994 | Andersen et al. | |
| 5,385,776 A | 1/1995 | Maxfield et al. | |
| 5,443,458 A | 8/1995 | Eury | |
| 5,443,500 A * | 8/1995 | Sigwart | 623/1.17 |
| 5,449,382 A * | 9/1995 | Dayton | 623/1.15 |
| 5,464,450 A * | 11/1995 | Buscemi et al. | 623/1.2 |
| 5,536,573 A | 7/1996 | Rubner et al. | |
| 5,549,664 A * | 8/1996 | Hirata et al. | 623/1.48 |
| 5,578,075 A * | 11/1996 | Dayton | 623/1.15 |
| 5,587,507 A | 12/1996 | Kohn et al. | |
| 5,591,222 A | 1/1997 | Susawa et al. | |
| 5,599,352 A | 2/1997 | Dinh et al. | |
| 5,605,696 A | 2/1997 | Eury et al. | |
| 5,624,411 A | 4/1997 | Tuch | |
| 5,629,077 A | 5/1997 | Turnlund et al. | |

(Continued)

FOREIGN PATENT DOCUMENTS

AU    739 507    11/1998

(Continued)

OTHER PUBLICATIONS

International Search Report and Written Opinion received in PCT/US2007/078475, mailed Feb. 4, 2009, 29 pages.

(Continued)

*Primary Examiner* — Alvin J Stewart
(74) *Attorney, Agent, or Firm* — Fish & Richardson P.C.

(57) ABSTRACT

Endoprostheses (e.g., stents) containing adjustable surfaces are disclosed.

14 Claims, 10 Drawing Sheets

U.S. PATENT DOCUMENTS

| | | | |
|---|---|---|---|
| 5,658,327 A | 8/1997 | Altman et al. | |
| 5,674,242 A | 10/1997 | Phan | |
| 5,690,670 A * | 11/1997 | Davidson | 606/198 |
| 5,697,967 A | 12/1997 | Dinh et al. | |
| 5,700,286 A | 12/1997 | Tartaglia et al. | |
| 5,716,981 A | 2/1998 | Hunter et al. | |
| 5,721,049 A * | 2/1998 | Marcolongo et al. | 428/370 |
| 5,725,570 A | 3/1998 | Heath | |
| 5,733,925 A | 3/1998 | Kunz et al. | |
| 5,749,880 A * | 5/1998 | Banas et al. | 606/198 |
| 5,769,883 A | 6/1998 | Buscemi et al. | |
| 5,776,184 A | 7/1998 | Tuch | |
| 5,780,807 A | 7/1998 | Saunders | |
| 5,788,626 A * | 8/1998 | Thompson | 623/1.15 |
| 5,788,979 A | 8/1998 | Alt et al. | |
| 5,800,511 A | 9/1998 | Mayer | |
| 5,824,048 A | 10/1998 | Tuch | |
| 5,830,217 A | 11/1998 | Ryan | |
| 5,837,007 A | 11/1998 | Altman et al. | |
| 5,837,275 A * | 11/1998 | Burrell et al. | 424/409 |
| 5,843,172 A | 12/1998 | Yan | |
| 5,869,140 A | 2/1999 | Blohowiak et al. | |
| 5,873,904 A | 2/1999 | Ragheb et al. | |
| 5,876,756 A | 3/1999 | Takada et al. | |
| 5,899,935 A | 5/1999 | Ding | |
| 5,935,506 A | 8/1999 | Schmitz et al. | |
| 5,972,027 A | 10/1999 | Johnson | |
| 5,976,454 A | 11/1999 | Sterzel et al. | |
| 5,980,566 A | 11/1999 | Alt et al. | |
| 6,001,125 A * | 12/1999 | Golds et al. | 623/23.7 |
| 6,013,591 A * | 1/2000 | Ying et al. | 501/1 |
| 6,027,742 A * | 2/2000 | Lee et al. | 424/422 |
| 6,071,305 A | 6/2000 | Brown et al. | |
| 6,096,070 A | 8/2000 | Ragheb et al. | |
| 6,099,561 A * | 8/2000 | Alt | 623/1.44 |
| 6,099,562 A | 8/2000 | Ding et al. | |
| 6,117,592 A | 9/2000 | Hoshino et al. | |
| 6,120,535 A * | 9/2000 | McDonald et al. | 623/1.39 |
| 6,120,660 A | 9/2000 | Chu et al. | |
| 6,132,463 A * | 10/2000 | Lee et al. | 600/36 |
| 6,143,370 A | 11/2000 | Panagiotou et al. | |
| 6,159,142 A | 12/2000 | Alt | |
| 6,168,602 B1 | 1/2001 | Ryan | |
| 6,180,222 B1 | 1/2001 | Schulz et al. | |
| 6,212,434 B1 | 4/2001 | Scheiner | |
| 6,214,037 B1 | 4/2001 | Mitchell et al. | |
| 6,240,616 B1 | 6/2001 | Yan | |
| 6,245,103 B1 | 6/2001 | Stinson | |
| 6,245,104 B1 | 6/2001 | Alt | |
| 6,251,980 B1 | 6/2001 | Lan et al. | |
| 6,253,443 B1 | 7/2001 | Johnson | |
| 6,258,117 B1 | 7/2001 | Camrud et al. | |
| 6,280,385 B1 | 8/2001 | Melzer et al. | |
| 6,287,332 B1 | 9/2001 | Bolz et al. | |
| 6,290,721 B1 | 9/2001 | Heath | |
| 6,290,722 B1 | 9/2001 | Wang | |
| 6,291,076 B1 | 9/2001 | Nakatsugawa | |
| 6,309,414 B1 | 10/2001 | Rolando et al. | |
| 6,338,739 B1 | 1/2002 | Datta et al. | |
| 6,358,276 B1 | 3/2002 | Edwin | |
| 6,368,658 B1 | 4/2002 | Schwarz et al. | |
| 6,379,383 B1 | 4/2002 | Palmaz et al. | |
| 6,383,214 B1 * | 5/2002 | Banas et al. | 623/1.14 |
| 6,387,121 B1 | 5/2002 | Alt | |
| 6,387,124 B1 | 5/2002 | Buscemi et al. | |
| 6,391,033 B2 | 5/2002 | Ryan | |
| 6,423,092 B2 | 7/2002 | Datta et al. | |
| 6,440,487 B1 | 8/2002 | Delfino et al. | |
| 6,447,540 B1 | 9/2002 | Fontaine et al. | |
| 6,475,477 B1 | 11/2002 | Kohn et al. | |
| 6,478,815 B1 | 11/2002 | Alt | |
| 6,479,146 B1 | 11/2002 | Caruso et al. | |
| 6,492,096 B1 | 12/2002 | Liu et al. | |
| 6,506,437 B1 | 1/2003 | Harish et al. | |
| 6,517,571 B1 * | 2/2003 | Brauker et al. | 623/1.13 |
| 6,524,334 B1 * | 2/2003 | Thompson | 623/1.13 |
| 6,530,949 B2 | 3/2003 | Konya et al. | |
| 6,537,312 B2 | 3/2003 | Datta et al. | |
| 6,545,097 B2 | 4/2003 | Pinchuk et al. | |
| 6,549,811 B2 * | 4/2003 | Stewart et al. | 607/116 |
| 6,589,286 B1 | 7/2003 | Litner | |
| 6,602,287 B1 | 8/2003 | Millare et al. | |
| 6,613,077 B2 | 9/2003 | Gilligan et al. | |
| 6,626,933 B1 | 9/2003 | Lau et al. | |
| 6,626,939 B1 * | 9/2003 | Burnside et al. | 623/1.38 |
| 6,627,321 B1 | 9/2003 | Ellingsen et al. | |
| 6,629,992 B2 | 10/2003 | Bigus et al. | |
| 6,652,582 B1 * | 11/2003 | Stinson | 623/1.39 |
| 6,676,987 B2 | 1/2004 | Zhong | |
| 6,689,160 B1 * | 2/2004 | Okuda et al. | 623/1.39 |
| 6,719,987 B2 * | 4/2004 | Langford et al. | 424/405 |
| 6,726,712 B1 | 4/2004 | Raeder-Devens | |
| 6,730,699 B2 | 5/2004 | Li et al. | |
| 6,743,388 B2 * | 6/2004 | Sridharan et al. | 264/205 |
| 6,753,071 B1 | 6/2004 | Pacetti | |
| 6,767,360 B1 | 7/2004 | Alt et al. | |
| 6,796,435 B2 | 9/2004 | Izumi | |
| RE38,653 E | 11/2004 | Igaki et al. | |
| 6,827,737 B2 * | 12/2004 | Hill et al. | 623/1.4 |
| 6,847,837 B1 | 1/2005 | Melzer et al. | |
| 6,854,172 B2 | 2/2005 | Kaese et al. | |
| 6,884,429 B2 | 4/2005 | Koziak et al. | |
| 6,887,270 B2 | 5/2005 | Miller et al. | |
| 6,887,857 B2 | 5/2005 | Naimark et al. | |
| 6,899,731 B2 | 5/2005 | Li et al. | |
| 6,908,506 B2 | 6/2005 | Zimmermann | |
| 6,913,765 B2 | 7/2005 | Li et al. | |
| 6,918,869 B2 | 7/2005 | Shaw et al. | |
| 6,921,390 B2 | 7/2005 | Bucay-Couto et al. | |
| 6,923,996 B2 | 8/2005 | Epstein et al. | |
| 6,951,053 B2 | 10/2005 | Padilla et al. | |
| 6,953,594 B2 | 10/2005 | Lee et al. | |
| 6,954,977 B2 * | 10/2005 | Maguire et al. | 29/460 |
| 6,964,817 B2 | 11/2005 | Date et al. | |
| 6,972,130 B1 * | 12/2005 | Lee et al. | 424/426 |
| 6,986,899 B2 * | 1/2006 | Hossainy et al. | 424/423 |
| 6,989,156 B2 * | 1/2006 | Gillis | 424/618 |
| 6,991,709 B2 | 1/2006 | Gopalraja et al. | |
| 7,011,670 B2 | 3/2006 | Radisch, Jr. | |
| 7,011,678 B2 | 3/2006 | Tenerz et al. | |
| 7,041,130 B2 | 5/2006 | Santini, Jr. et al. | |
| 7,048,767 B2 * | 5/2006 | Namavar | 623/23.6 |
| 7,060,240 B2 * | 6/2006 | Costa et al. | 423/338 |
| 7,070,576 B2 | 7/2006 | O'Brien et al. | |
| 7,078,108 B2 * | 7/2006 | Zhang et al. | 428/579 |
| 7,108,716 B2 * | 9/2006 | Burnside et al. | 623/1.38 |
| 7,157,096 B2 * | 1/2007 | Zhang et al. | 424/422 |
| 7,241,295 B2 * | 7/2007 | Maguire | 606/41 |
| 7,261,732 B2 * | 8/2007 | Justino | 623/1.24 |
| 7,267,960 B2 * | 9/2007 | Galibert et al. | 435/7.1 |
| RE40,122 E * | 2/2008 | Thompson | 623/1.13 |
| 7,331,993 B2 * | 2/2008 | White | 623/2.12 |
| 7,344,560 B2 * | 3/2008 | Gregorich et al. | 623/1.15 |
| 7,462,366 B2 | 12/2008 | Lanphere et al. | |
| 7,537,610 B2 * | 5/2009 | Reiss | 623/1.39 |
| 7,713,297 B2 * | 5/2010 | Alt | 623/1.39 |
| 7,749,264 B2 * | 7/2010 | Gregorich et al. | 623/1.15 |
| 7,771,773 B2 * | 8/2010 | Namavar | 427/2.1 |
| 2001/0013166 A1 | 8/2001 | Yan | |
| 2001/0021871 A1 | 9/2001 | Stinson | |
| 2001/0029660 A1 | 10/2001 | Johnson | |
| 2001/0032014 A1 | 10/2001 | Yang et al. | |
| 2002/0000406 A1 | 1/2002 | Izumi | |
| 2002/0004060 A1 | 1/2002 | Heublein et al. | |
| 2002/0032477 A1 | 3/2002 | Helmus et al. | |
| 2002/0035394 A1 | 3/2002 | Fierens et al. | |
| 2002/0065553 A1 | 5/2002 | Weber | |
| 2002/0090313 A1 | 7/2002 | Wang et al. | |
| 2002/0099434 A1 | 7/2002 | Buscemi et al. | |
| 2002/0111694 A1 | 8/2002 | Ellingsen et al. | |
| 2002/0123801 A1 | 9/2002 | Pacetti et al. | |
| 2002/0133224 A1 | 9/2002 | Bajgar et al. | |
| 2002/0138154 A1 | 9/2002 | Li et al. | |
| 2002/0144757 A1 | 10/2002 | Craig et al. | |
| 2002/0165578 A1 | 11/2002 | Sawitowski et al. | |
| 2003/0003220 A1 | 1/2003 | Zhong et al. | |
| 2003/0004564 A1 * | 1/2003 | Elkins et al. | 623/1.15 |

| | | | | | | |
|---|---|---|---|---|---|---|
| 2003/0018380 A1 | 1/2003 | Craig et al. | | 2006/0025848 A1 | 2/2006 | Weber et al. |
| 2003/0033007 A1 | 2/2003 | Sirhan et al. | | 2006/0038027 A1 | 2/2006 | O'Connor et al. |
| 2003/0044596 A1 | 3/2003 | Lazarov et al. | | 2006/0041182 A1 | 2/2006 | Forbes et al. |
| 2003/0060873 A1 | 3/2003 | Gertner et al. | | 2006/0052863 A1 | 3/2006 | Harder et al. |
| 2003/0068355 A1 | 4/2003 | Shanley et al. | | 2006/0052864 A1 | 3/2006 | Harder et al. |
| 2003/0069631 A1 | 4/2003 | Stoll | | 2006/0058868 A1* | 3/2006 | Gale et al. .................. 623/1.15 |
| 2003/0077200 A1 | 4/2003 | Craig et al. | | 2006/0064160 A1 | 3/2006 | Gerold et al. |
| 2003/0083646 A1 | 5/2003 | Sirhan et al. | | 2006/0067908 A1 | 3/2006 | Ding |
| 2003/0088307 A1 | 5/2003 | Shulze et al. | | 2006/0085065 A1 | 4/2006 | Krause et al. |
| 2003/0100815 A1 | 5/2003 | Da Silva et al. | | 2006/0088653 A1 | 4/2006 | Chappa et al. |
| 2003/0104030 A1 | 6/2003 | Igaki et al. | | 2006/0100696 A1 | 5/2006 | Atanasoska et al. |
| 2003/0120339 A1 | 6/2003 | Banik et al. | | 2006/0118236 A1* | 6/2006 | House et al. ................. 156/294 |
| 2003/0125803 A1 | 7/2003 | Vallana | | 2006/0122694 A1 | 6/2006 | Stinson et al. |
| 2003/0143330 A1 | 7/2003 | Loomis et al. | | 2006/0122697 A1 | 6/2006 | Shanley et al. |
| 2003/0185895 A1 | 10/2003 | Lanphere | | 2006/0124472 A1 | 6/2006 | Rokicki |
| 2003/0204239 A1 | 10/2003 | Carlyle et al. | | 2006/0129222 A1 | 6/2006 | Stinson |
| 2003/0211135 A1 | 11/2003 | Greenhalgh et al. | | 2006/0149352 A1 | 7/2006 | Schlun |
| 2003/0221307 A1 | 12/2003 | Kaese et al. | | 2006/0153729 A1 | 7/2006 | Stinson et al. |
| 2003/0228523 A1 | 12/2003 | DeLongchamp et al. | | 2006/0193892 A1 | 8/2006 | Furst et al. |
| 2003/0236513 A1 | 12/2003 | Schwarz et al. | | 2006/0198869 A1 | 9/2006 | Furst et al. |
| 2004/0000046 A1 | 1/2004 | Stinson | | 2006/0200233 A1* | 9/2006 | Kujawski .................... 623/1.49 |
| 2004/0022939 A1 | 2/2004 | Kim et al. | | 2006/0212108 A1 | 9/2006 | Tittelbach |
| 2004/0034409 A1 | 2/2004 | Heublein et al. | | 2006/0229711 A1 | 10/2006 | Yan et al. |
| 2004/0039438 A1 | 2/2004 | Alt | | 2006/0241739 A1 | 10/2006 | Besselink et al. |
| 2004/0073155 A1 | 4/2004 | Laufer et al. | | 2006/0259133 A1* | 11/2006 | Sowinski et al. ............. 623/1.54 |
| 2004/0073293 A1 | 4/2004 | Thompson | | 2006/0264138 A1* | 11/2006 | Sowinski et al. ............. 442/315 |
| 2004/0082682 A1 | 4/2004 | Loomis et al. | | 2006/0271156 A1* | 11/2006 | Ledergerber ................. 623/1.13 |
| 2004/0088038 A1 | 5/2004 | Dehnad et al. | | 2006/0271168 A1 | 11/2006 | Kleine et al. |
| 2004/0098108 A1 | 5/2004 | Harder et al. | | 2006/0271192 A1 | 11/2006 | Olsen et al. |
| 2004/0106975 A1 | 6/2004 | Solovay et al. | | 2006/0276884 A1* | 12/2006 | Lye et al. .................... 623/1.39 |
| 2004/0137039 A1 | 7/2004 | Sukhishvili et al. | | 2006/0276885 A1* | 12/2006 | Lye et al. .................... 623/1.39 |
| 2004/0138738 A1 | 7/2004 | Stinson | | 2007/0003596 A1 | 1/2007 | Tittelbach et al. |
| 2004/0143317 A1 | 7/2004 | Stinson et al. | | 2007/0020306 A1 | 1/2007 | Schultheiss |
| 2004/0158310 A1 | 8/2004 | Weber et al. | | 2007/0050007 A1* | 3/2007 | Kondyurin et al. .......... 623/1.13 |
| 2004/0181278 A1 | 9/2004 | Tseng et al. | | 2007/0123131 A1* | 5/2007 | Nguyen et al. ............... 442/408 |
| 2004/0182511 A1* | 9/2004 | Rakos et al. .................. 156/287 | | 2007/0123973 A1 | 5/2007 | Roth et al. |
| 2004/0220659 A1 | 11/2004 | Girton | | 2007/0129792 A1 | 6/2007 | Picart et al. |
| 2004/0220660 A1 | 11/2004 | Shanley et al. | | 2007/0135908 A1 | 6/2007 | Zhao |
| 2004/0230290 A1 | 11/2004 | Weber et al. | | 2007/0141106 A1 | 6/2007 | Bonutti et al. |
| 2004/0249440 A1 | 12/2004 | Bucker et al. | | 2007/0142899 A1 | 6/2007 | Lootz et al. |
| 2004/0249443 A1 | 12/2004 | Shanley et al. | | 2007/0191923 A1 | 8/2007 | Weber |
| 2005/0004661 A1 | 1/2005 | Lewis et al. | | 2007/0191931 A1 | 8/2007 | Weber |
| 2005/0010275 A1 | 1/2005 | Sahatjian | | 2007/0207186 A1* | 9/2007 | Scanlon et al. ............... 424/424 |
| 2005/0010279 A1 | 1/2005 | Tenerz et al. | | 2007/0250156 A1* | 10/2007 | Palmaz ........................ 623/1.39 |
| 2005/0027350 A1 | 2/2005 | Momma et al. | | 2007/0282432 A1 | 12/2007 | Stinson et al. |
| 2005/0033407 A1 | 2/2005 | Weber et al. | | 2008/0003431 A1* | 1/2008 | Fellinger et al. .............. 428/375 |
| 2005/0038134 A1 | 2/2005 | Loomis et al. | | 2008/0033536 A1 | 2/2008 | Wittchow |
| 2005/0038501 A1 | 2/2005 | Moore, Jr. et al. | | 2008/0051866 A1* | 2/2008 | Chen et al. ................... 623/1.11 |
| 2005/0042440 A1 | 2/2005 | Bach et al. | | 2008/0082162 A1 | 4/2008 | Boismier et al. |
| 2005/0055044 A1 | 3/2005 | Kangas | | 2008/0086199 A1* | 4/2008 | Dave et al. ................... 623/1.42 |
| 2005/0060021 A1* | 3/2005 | O'Brien et al. ............... 623/1.15 | | 2008/0097577 A1 | 4/2008 | Atanasoska et al. |
| 2005/0064088 A1 | 3/2005 | Fredrickson | | 2008/0124373 A1* | 5/2008 | Xiao et al. .................... 424/423 |
| 2005/0070990 A1 | 3/2005 | Stinson | | 2008/0183277 A1 | 7/2008 | Atanasoska et al. |
| 2005/0071016 A1 | 3/2005 | Hausdorf et al. | | 2008/0290467 A1 | 11/2008 | Shue |
| 2005/0079132 A1 | 4/2005 | Wang et al. | | 2008/0294246 A1 | 11/2008 | Scheuermann |
| 2005/0107869 A1 | 5/2005 | Sirhan et al. | | 2009/0022771 A1* | 1/2009 | Lynn et al. .................... 424/423 |
| 2005/0107870 A1* | 5/2005 | Wang et al. .................. 623/1.44 | | | | |
| 2005/0129727 A1 | 6/2005 | Weber et al. | | | | |
| 2005/0131528 A1 | 6/2005 | Buscemi et al. | | | | |
| 2005/0149170 A1 | 7/2005 | Tassel et al. | | | | |
| 2005/0149177 A1 | 7/2005 | Weber et al. | | | | |
| 2005/0159805 A1 | 7/2005 | Weber et al. | | | | |
| 2005/0159809 A1 | 7/2005 | Hezi-Yamit et al. | | | | |
| 2005/0163821 A1 | 7/2005 | Sung et al. | | | | |
| 2005/0165301 A1 | 7/2005 | Smith et al. | | | | |
| 2005/0165470 A1 | 7/2005 | Weber | | | | |
| 2005/0169969 A1 | 8/2005 | Li et al. | | | | |
| 2005/0177226 A1 | 8/2005 | Banik et al. | | | | |
| 2005/0182361 A1 | 8/2005 | Lennox | | | | |
| 2005/0187611 A1 | 8/2005 | Ding et al. | | | | |
| 2005/0192657 A1 | 9/2005 | Colen et al. | | | | |
| 2005/0192662 A1 | 9/2005 | Ward | | | | |
| 2005/0216074 A1 | 9/2005 | Sahatjian | | | | |
| 2005/0234538 A1 | 10/2005 | Litvack et al. | | | | |
| 2005/0251249 A1 | 11/2005 | Sahatjian | | | | |
| 2005/0261760 A1 | 11/2005 | Weber | | | | |
| 2005/0283229 A1 | 12/2005 | Dugan et al. | | | | |
| 2006/0002979 A1 | 1/2006 | Ashammakhi et al. | | | | |
| 2006/0014039 A1* | 1/2006 | Zhang et al. .................. 428/615 | | | | |

FOREIGN PATENT DOCUMENTS

| | | |
|---|---|---|
| AU | 2003 203 722 | 11/2003 |
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 10 2006 38236 | 2/2008 |
| EP | 0 006 544 | 6/1979 |
| EP | 0 337 035 | 10/1989 |
| EP | 0 923 389 | 7/1998 |
| EP | 0 923 912 | 6/1999 |
| EP | 0 966 979 | 12/1999 |
| EP | 0 972 563 | 1/2000 |
| EP | 1 222 901 | 7/2002 |
| EP | 1 260 214 | 11/2002 |
| EP | 1 273 314 | 1/2003 |
| EP | 1 389 471 | 2/2004 |
| EP | 1 733 746 | 12/2006 |
| EP | 1 750 780 | 10/2007 |
| RU | 2 218 242 | 12/2003 |

| | | |
|---|---|---|
| WO | WO 93/04118 | 3/1993 |
| WO | WO 97/11724 | 4/1997 |
| WO | WO 98/48851 | 11/1998 |
| WO | 99/47077 | 9/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | WO 00/66190 | 11/2000 |
| WO | WO 01/49338 | 7/2001 |
| WO | WO 01/78906 | 10/2001 |
| WO | WO 02/45764 | 6/2002 |
| WO | WO 02/47739 | 6/2002 |
| WO | WO 02/053202 | 7/2002 |
| WO | 03/002243 | 1/2003 |
| WO | WO 03/013396 | 2/2003 |
| WO | 03/035131 | 5/2003 |
| WO | WO 03/035278 | 5/2003 |
| WO | WO 03/063733 | 8/2003 |
| WO | WO 03/094990 | 11/2003 |
| WO | WO 2004/093643 | 11/2004 |
| WO | WO 2005/065576 | 7/2005 |
| WO | WO 2005/110395 | 11/2005 |
| WO | WO 2005/118019 | 12/2005 |
| WO | WO 2006/008739 | 1/2006 |
| WO | 2006/065356 | 6/2006 |
| WO | WO 2006/060033 | 6/2006 |
| WO | WO 2006/060534 | 6/2006 |
| WO | 2006/077154 | 7/2006 |
| WO | WO 2006/108065 | 10/2006 |
| WO | WO 2007/005806 | 1/2007 |
| WO | 2007/013102 | 2/2007 |
| WO | WO 2007/018931 | 2/2007 |
| WO | 2007/035791 | 3/2007 |
| WO | WO 2007/024552 | 3/2007 |
| WO | 2007/079636 | 7/2007 |
| WO | WO 2007/082147 | 9/2007 |
| WO | WO 2008/062414 | 5/2008 |
| WO | WO 2008/117315 | 10/2008 |

OTHER PUBLICATIONS

Mohanty, M. et al. "Evaluation of soft tissue response to a poly[urethane urea]" *BioMaterials, Elsevier Science Publishers*. Jan. 1, 1992, 13(10) 651-656.
U.S. Appl. No. 10/849,742, filed May 20, 2004, Chen et al.
U.S. Appl. No. 60/826,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.
"Galvanic cell" printout from wikipedia, 2 pgs, printed Oct. 28, 2005.
"Galvanic corrosion", http://www.corrosion-doctors.org/Aircraft/galvdefi.htm, 3 pgs., printed Oct. 28, 2005.
"Galvanic series" printout from Wikipedia, p. 1 of 2, printed Oct. 28, 2005.
"Best of the ACC Scientific Session 2002," *Rev. Cardiovasc. Med.*, 2002, 3(2):85-104.
"Corrosion Theory and Corrosion Protection," *EM 1110-2-3400*, 1995, 8 pages.
Aghion et al., "Newly Developed Magnesium Alloys for Powertrain Applications," *JOM*, 2003, p. 30.
Andión et al., "Corrosion behaviour at the interface of steel bars embedded in cement slurries. Effect of phenol polymer coatings," *Corrosion Science*, 2002, 44:2805-2816.
Antipov et al., "Polyelectrolyte Multilayer Capsules as Vehicles with Tunable Permeability," *Advances in Colloid and Interface Science*, 2004, 111:49-61.
Arts et al., "Polyphenols and disease risk in epidemiologic studies," *Am. J. Clin. Nutr.*, 2005, 81:317S-325S.
Artyukhin et al., "Layer-by-Layer Electrostatic Self-Assembly of Polyelectrolyte Nanoshells on Individual Carbon Nanotube Templates," *Langmuir*, 2004, 20:1442-1448.
Bach et al., "Corrosion Protection and Repassivation After the Deformation of Magnesium Alloys Coated With a Protective Magnesium Fluoride Layer," *JOM*, 2004, p. 343.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Baurschmidt et al., "The Electrochemical Aspects of the Thrombogenicity of a Material," *J. Bioengineering*, 1977, 1:261-278.
Berkland et al., "Controlling Surface Nano-structure Using Flow-Limited Field-Injection Electrostatic Spraying (FFESS) of poly(D,L-lactide-co-glycolide)," *Biomaterials*, 2004, 25:5649-5658.
Berry et al., "Functionalisation of magnetic nanoparticles for applications in biomedicine," *J. Phys. D: Appl. Phys.*, 2003, 36:R198-R206.
Bolz et al., "Effect of smooth, porous and fractal surface structure on the properties of an interface," *J. Materials Science: Materials in Medicine*, 1995, 6:844-848.
Brandau et al., "Nanoporous Ceramic Coatings for Synthesis of Radioactive Implants," *Journal of Nuclear Medicine Abstract Book*, Jun. 7, 2000, p. 244P, Abstract No. 1076.
Brückner et al., "Metal plasma immersion ion implantation and deposition (MPIIID): chromium on magnesium," *Surface and Coatings Technology*, 1998, 103-104:227-230.
Buescher et al., "Characterization of Wet-Chemically Nanostructured Stainless Steel Surfaces," *Mat. Res. Soc. Symp. Proc.*, 2001, 676:1-6.
Caruso et al., "Ultrathin Molybdenum Polyoxometalate-Polyelectrolyte Multilayer Films," *Langmuir*, 1998, 14:3462-3465.
Casan-Pastor et al., "Polyoxometalates: From Inorganic Chemistry to Materials Science," *Frontiers in Bioscience*, 2004, 9:1759-1770.
Chaieb et al., "Inhibition of the corrosion of steel in 1 M HCl by eugenol derivatives," *Applied Surface Science*, 2005, 246:199-206.
Changwen et al., "Polyoxometalate-based organic-inorganic hybrid materials"; http://www.solgel.com/articles/oct01/echangwen.asp, Retrieved from the Internet on Nov. 1, 2004 (17 pages).
Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.
International Search Report/Written Opinion in PCT/US05/16600 mailed May 4, 2006, 15 pages.
International Preliminary Report on Patentability in PCT/US05/16600 mailed Nov. 30, 2006, 7 pages.
International Preliminary Report on Patentability in PCT/US07/78476 mailed Mar. 26, 2009, 7 pages.
Authorized Officer Simin Baharlou, International Search Report/Written Opinion in PCT/US07/66568 mailed Oct. 8, 2007, 11 pages.
Authorized Officer Simin Baharlou, International Preliminary Report on Patentability in PCT/US07/66568 mailed Oct. 23, 2008, 10 pages.
International Search Report/Written Opinion in PCT/US07/78505 mailed Mar. 4, 2008, 10 pages.
International Preliminary Report on Patentability in PCT/US07/78505 mailed Mar. 26, 2009, 7 pages.
Authorized Officer Athina Nickitas-Etienne, International Search Report/Written Opinion in PCT/US07/78449, mailed Jan. 13, 2009, 24 pages.
Authorized Officer Athina Nickitas-Etienne, International Preliminary Report on Patentability in PCT/US07/78449 mailed Mar. 26, 2009, 9 pages.
Authorized Officer Simin Baharlou, International Search Report/Written Opinion in PCT/US07/75072 mailed Jan. 25, 2008, 11 pages.
Authorized Officer Simin Baharlou, International Preliminary Report on Patentability in PCT/US07/75072 mailed Feb. 12, 2009, 9 pages.
International Search Report/Written Opinion in PCT/US07/78429 mailed Mar. 28, 2008, 13 pages.
International Preliminary Report on Patentability in PCT/US07/78429 mailed Apr. 2, 2009, 8 pages.
International Search Report/Written Opinion in PCT/US07/78411 mailed Mar. 6, 2008, 12 pages.
International Preliminary Report on Patentability in PCT/US07/78411 mailed Feb. 4, 2009, 8 pages.
Authorized Officer Elisabeth Reinecke, International Search Report/Written Opinion in PCT/US07/60137 mailed Jul. 27, 2007, 20 pages.

Authorized Officer Elisabeth Reinecke, International Preliminary Report on Patentability in PCT/US07/60137 mailed Jul. 17, 2008, 7 pages.

International Preliminary Report on Patentability in PCT/US07/78412 mailed Apr. 2, 2009, 7 pages.

Authorized Officer Trudy Hinterwimmer, International Search Report/Written Opinion in PCT/US07/78412 mailed Mar. 3, 2008, 10 pages.

Authorized Officer Joëlle Gerber, International Search Report/Written Opinion in PCT/US07/78450 mailed Nov. 19, 2008, 17 pages.

International Preliminary Report on Patentability in PCT/US07/78450 mailed Mar. 26, 2009, 7 pages.

International Search Report/Written Opinion in PCT/US07/73839 mailed Apr. 16, 2008, 17 pages.

International Preliminary Report on Patentability in PCT/US07/73839 mailed 2 Apr. 2, 2009, 10 pages.

Authorized Officer Cecilia Giel-Barragán Ramos, International Search Report/Written Opinion in PCT/US07/79841 mailed Feb. 4, 2009, 21 pages.

Authorized Officer Athina Nickitas-Etienne, International Preliminary Report on Patentability in PCT/US07/79841 mailed Apr. 30, 2009, 7 pages.

Authorized Officer Joëlle Gerber, International Search Report/Written Opinion in PCT/US07/88888 mailed Jul. 13, 2009, 24 pages.

Authorized Officer Nora Lindner, International Preliminary Report on Patentability in PCT/US07/88888 mailed Jul. 30, 2009, 11 pages.

Authorized Officer Véronique van Loon-Mégard, International Search Report/Written Opinion in PCT/US08/75976 mailed Nov. 25, 2008, 20 pages.

Authorized Officer Trudy Hinterwimmer, International Search Report/Written Opinion in PCT/US09/49422 mailed Aug. 24, 2009, 10 pages.

Damiani et al., "Vasorelaxant effects on eugenol on rat thoracic aorta," *Vascular Pharmacol.*, 2003, 40:59-66.

Dexter, "Galvanic Corrosion," MAS Note, University of Delaware Sea Grant Marine Advisory Service, 2003.

Di Mario et al., "MOONLIGHT: a controlled registry of an iridium-oxide coated stent with angiographic follow up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duygu, "Controlled Release Systems," http://www.biomed.metu.edu.tr/courses/term_papers/contr-rel-sys_duygu.htm (Dec. 30, 2005).

Eniola and Hammer, "Characterization of biodegradable drug delivery vehicles with the adhesive properties of leukocytes II: effect of degradation on targeting activity," *Biomaterials*, 2005, 26:661-670.

Farhat et al., "Corrosion Control Using Polyelectrolyte Multilayers," *Electrochemical and Solid State Letters*, 2002, 5(4):B13-B15.

Ferrando, "Review of Corrosion and Corrosion Control of Magnesium Alloys and Composites," *J. Mater. Eng.*, 1989, 11:299-313.

Fischer et al., "Hydrogen in magnesium alloys and magnesium interfaces: preparation, electronic properties and interdiffusion," *J. Less Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Frei, "On the Role of Vitamin C and Other Antioxidants in Atherogenesis and Vascular Dysfunction," *Proceedings—Society for Experimental Biology and Medicine*, 1999, 222:196-204.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Gray and Luan, "Protective coatings on magnesium and its alloys—a critical review," *J. Alloys Compounds*, 2002, 336:88-113.

Guo et al., "Multi-layer LB films of single-wall carbon nanotubes," *Physica B*, 2002, 323:235-236.

Gurib-Fakim, "Medicinal plants: Traditions of yesterday and drugs of tomorrow," *Molecular Aspects of Medicine*, 2006, 27:1-93.

Haferkamp et al., "Magnesium-Base-Alloys as Implant-Material Steps to the Production of Thin Components," *Magnesium*, 2000, 159-164.

Hau et al., "Surface-Chemistry Technology for Microfluidics," *J. Micromech. Microeng.*, 2003.13:272-278.

Heublein et al., "Biocorrosion of magnesium alloys: a new principle in cardiovascular implant technology?" *Heart*, 2003, 89:651-656.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Local Tissue Engineering by Biocorrosion Vision or Reality?" *The American Journal of Cardiology, TCT Abstracts/Poster*, Oct. 16, 2000.

Huang et al., "A Review on Polymer Nanofibers by Electro-spinning and their Applications in Nanocomposites," *Composites Science & Technology*, 2003, 63:2223-2253.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend," *Experimental Pathology and Parasitology*, 2000, 4:49-59.

Jiang, "A review of wet impregnation—An alternative method for the fabrication of high performance and nano-structured electrodes of solid oxide fuel cells," *Materials Science and Engineering A*, 2006, 418:199-210.

Kean and Davies, "Cathodic Protection," 7 pages, 1981; http://www.npl.co.uk/upload/pdf/cathodic_protection.pdf.

Kim et al., "Comprehensive study on vitamin C equivalent antioxidant capacity (VCEAC) of various polyphenols in scavenging a free radical its structural relationship," *Crit. Rev. Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydrides: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

Lambert et al., "Inhibition of carcinogenesis by polyphenols: evidence from laboratory investigations," *Am. J. Clin. Nutr.*, 2005, 81:284S-291S.

Lee et al., "Retentive and compressive strengths of modified zinc oxide-eugenol cements," *J. Dentistry*, 2000, 28:69-75.

Liao et al., "Fabrication of porous biodegradable polymer scaffolds using a solvent merging/particulate leaching method," *J. Biomed. Mater. Res.*, 2002, 59(4):676-681.

Lin et al., "Micropatterning proteins and cells on polylactic acid and poly(lactide-*co*-glycolide)," *Biomaterials*, 2005, 26:3655-3662.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Maier et al., "High concentrations of magnesium modulate vascular endothelial cell behaviour in vitro," *Biochim. Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetite Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81:277S-283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001.

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2006, 44:1485-1495.

Park et al., "Microstructural change and precipitation hardening in melt-spun Mg-X-Ca alloys," *Science and Technology of Advanced Materials*, 2001, 2:73-78.

Peuster et al., "Long-term biocompatibility of a corrodible peripheral iron stent in the porcine of descending aorta," *Biomaterials*, 2006, 27:4955-4962.

Peuster et al., "A novel approach to temporary stenting: degradable cardiovascular stents produced from corrodible metal-results 6-18 months after implantation into New Zealand white rabbits," *Heart*, 2001, 86:563-569.

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schetky, "Shape Memory Alloys," *Encyclopedia of Chemical Technology* (3rd ed.), 1962, John Wiley & Sons, 20:726.

Shaw, "Corrosion Resistance of Magnesium Alloys," *ASM Handbook vol. 13A: Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning: the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*, 2001, 383:224-226.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The Photochemistry of Chromium, Manganese, and Iron Porphyrin Complexes," Complexes, *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80: 179-195.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Wallerath et al., "A blend of polyphenols explains the stimulatory effect of red wine on human endothelial NO synthase," *Nitric Oxide*, 2005, 12(2):97-104.

Wan et al., "Influence of Plasma Immersion Ion Implantation on Corrosion Properties of Magnesium," South Jiaotong University, Chengdu, 2005.

Wang et al., "Nonlinear optical properties of thin iron films grown on MgO (100) by uplsed laser deposition," *Thin Solid Films*, 2005, 471:86-90.

Wang et al., "Characterisation of Severely Deformed Austenitic Stainless Steel Wire," *Materials Science and Technology*, 2005, 21:1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271:407-415.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Williamson et al., "Bioavailability and bioefficacy of polyphenols in humans. II. Review of 93 intervention studies," *Am. J. Clin. Nutr.*, 2005, 81:243S-255S.

Witte et al., "In vitro and in vivo corrosion measurements of magnesium alloys," *Biomaterials*, 2006, 27:1013-1018.

Yamaguchi et al., "Mg2Si Coating Technology on Magnesium Alloys to Improve Corrosion and Wear Resistance", *JOM*, 2004, p. 343.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta Mat.*, 2000, 42:1089-1094.

Yu and Uan, "Sacrificial Mg film anode for cathodic protection of die cast Mg-9-wt.%-1 wt.%Zn alloy in NaC1 aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Mat.*, 1998, 38(2):191-198.

Zeta Potential-An Introduction in 30 Minutes, Technical Note; http://www.nbtc.cornell.edu/facilities/downloads/Zeta%20potential%20-%20An%20introduction%20in%2030in%20minutes.pdf, Retrieved from the Internet on May 9, 2005 (6 pages).

Zhang et al., "Natural Polyelectrolyte Films Based on Layer-by-Layer Deposition of Collagen and Hyaluronic Acid," *Biomaterials*, 2005, 26:3353-3361.

Zhang et al., "Improving multilayer films endurance by photoinduced interaction between Dawson-type polyoxometalate and diazo resin," *Materials Chemistry and Physics*, 2005, 90:57-52.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zhou et al., "Drug-loaded, Magnetic, hollow silica nanocomposites for nanomedicine," *Nanomedicine: Nanotechnology, Biology and Medicine*, 2005, 1:233-237.

Zucchi et al., "Influence of a silane treatment on the corrosion resistance of a WE43 magnesium alloy," *Surface Coatings Technol.*, 2006, 200:4136-4143.

European, International Preliminary Report on Patentability in Application No. PCT/US2007/078475, mailed Mar. 26, 2009, 8 pages.

* cited by examiner

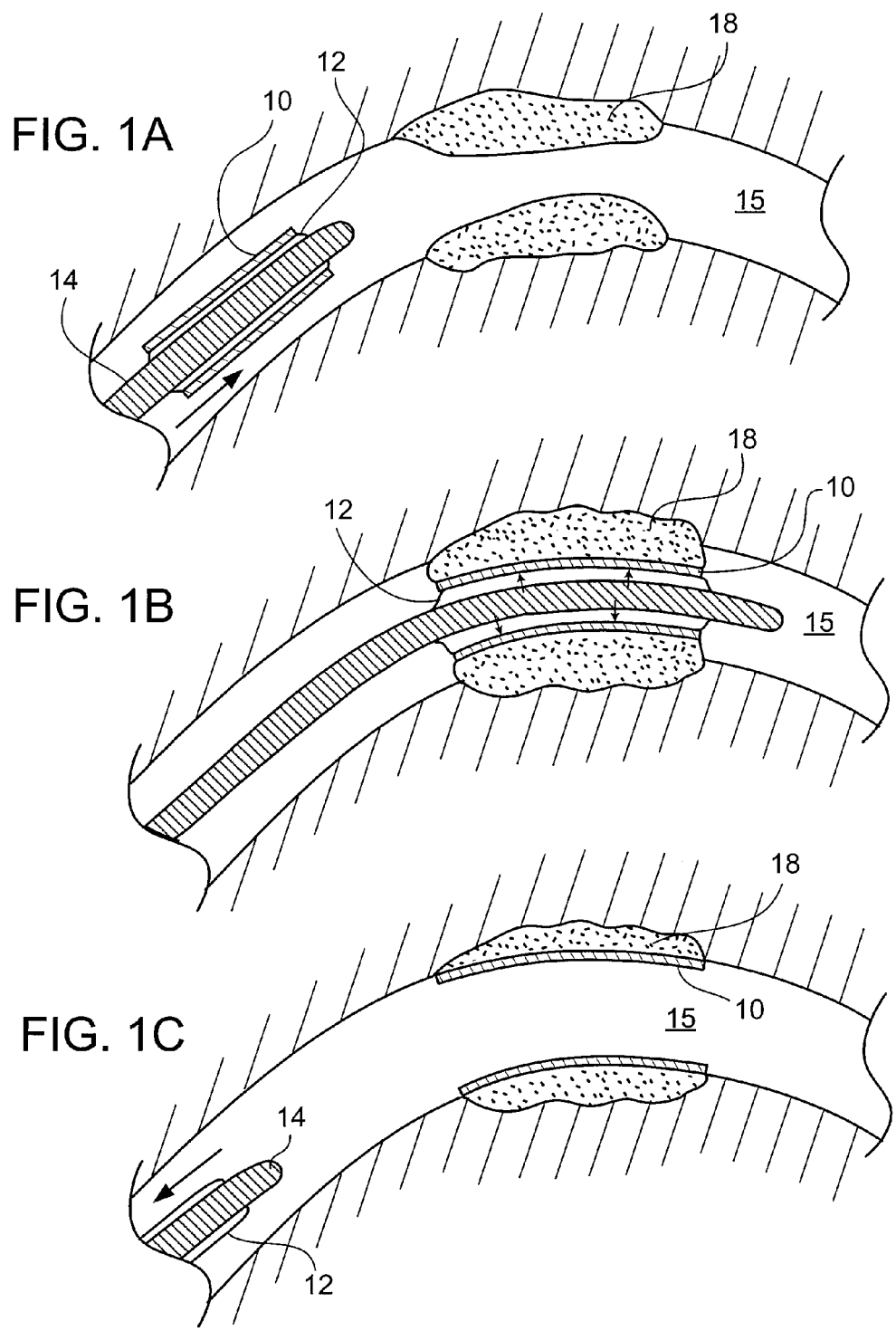

ENDOPROSTHESIS WITH ADJUSTABLE SURFACE FEATURES

CROSS-REFERENCE TO RELATED APPLICATIONS

This application claims priority under 35 USC §119(e) to U.S. Provisional Patent Application Ser. No. 60/845,047, filed on Sep. 15, 2006, the entire contents of which are hereby incorporated by reference.

TECHNICAL FIELD

This invention relates to medical devices, such as endoprostheses, and methods of making and using the same.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses can be delivered inside the body by a catheter. Typically the catheter supports a reduced-size or compacted form of the endoprosthesis as it is transported to a desired site in the body, for example, the site of weakening or occlusion in a body lumen. Upon reaching the desired site, the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

SUMMARY

In one aspect, the invention features an endoprosthesis, e.g., a stent, having a surface or portion thereof that includes a polymer having a morphology of surface features having a substantially uniform periodicity of about 1 to 50 microns (e.g., about 15 to 25 microns).

In another aspect, the invention features a method of forming a stent that includes providing the stent with a polymer morphology having surface features having a substantially uniform periodicity of about 1 to 50 microns (e.g., about 15 to 25 microns), by applying a solution to the polymer.

Embodiments may include one or more of the following features. The endoprosthesis, e.g., stent, has surface features that include a plurality of nodules, e.g., nodules having one or more of the following features: a nodule diameter of about 5 to 50 microns (e.g., about 19 microns); a nodule height of less than 50 microns, e.g., about 1 to 10 microns; a nodule density of about 0.0025 nodules per square micron; and/or nodules defining regions therebetween having a width of about 50 to 2000 nm. In embodiments, the nodules are arranged in substantially parallel rows, e.g., arranged radially in substantially parallel rows. In embodiments, the endoprosthesis, e.g., stent, has surface features that include one or more rib-forms, e.g., rib-forms about 500 to 2500 nm in depth; having a periodicity of less than about 50 microns; and/or rib-forms defining regions therebetween having a width of about 50 to 2000 nm. The endoprosthesis, e.g., stent, can have a combination of surface features that includes nodules and rib-forms. For example, the surface features can be porous, e.g., a porous polymer and/or can include one or more elongated grooves. In embodiments, the polymer further includes a therapeutic agent; is bioerodible; and/or is a layer on the endoprosthesis, e.g., stent, surface (e.g., a metal or a polymer layer on the endoprosthesis, e.g., stent, surface). In other embodiments, the endoprosthesis, e.g., stent, has a polymer body. In yet other embodiments, the morphology is formed by the same polymer as the polymer body.

Further embodiments may include one or more of the following features. The endoprosthesis, e.g., stent, is formed by a method that includes one or more of, e.g., controlling the evaporation rate and/or volatility of the solution (e.g., using a solution mixture of solvents having a boiling point in the range of about 50° C. to about 180° C.); applying the solution (e.g., a solution that includes the polymer) to the stent; applying the solution by spraying; controlling the size and/or velocity of the drops in the spray; controlling the surface energy of the solution, e.g., surface energy in the range of about 26 to 34 mJ/m$^2$. In embodiments, the solution further includes a surfactant and/or a therapeutic agent. In embodiments, nodule and/or rib-form surface features are formed. Embodiments may additionally include one or more of the following features: controlling the nodule size, e.g., by controlling the evaporation rate and/or surface energy of the solution; applying the solution by spraying and controlling the nodule size by controlling the size and/or velocity of the drops in the spray; controlling the rib form features by forming micelles in the solution; or masking at least a portion of the endoprosthesis, e.g., stent, to form morphological features.

Endoprostheses, e.g., stents, made by the methods described herein are also within the scope of the invention.

An erodible or bioerodible medical device, e.g., a stent, refers to a device, or a portion thereof, that exhibits substantial mass or density reduction or chemical transformation, after it is introduced into a patient, e.g., a human patient. Mass reduction can occur by, e.g., dissolution of the material that forms the device and/or fragmenting of the device. Chemical transformation can include oxidation/reduction, hydrolysis, substitution, electrochemical reactions, addition reactions, or other chemical reactions of the material from which the device, or a portion thereof, is made. The erosion can be the result of a chemical and/or biological interaction of the device with the body environment, e.g., the body itself or body fluids, into which it is implanted and/or erosion can be triggered by applying a triggering influence, such as a chemical reactant or energy to the device, e.g., to increase a reaction rate. For example, a device, or a portion thereof, can be formed from an active metal, e.g., Mg or Ca or an alloy thereof, and which can erode by reaction with water, producing the corresponding metal oxide and hydrogen gas (a redox reaction). For example, a device, or a portion thereof, can be formed from an erodible or bioerodible polymer, or an alloy or blend erodible or bioerodible polymers which can erode by hydrolysis with water. The erosion occurs to a desirable extent in a time frame that can provide a therapeutic benefit. For example, in embodiments, the device exhibits substantial mass reduction after a period of time which a function of the device, such as support of the lumen wall or drug delivery is no longer needed or desirable. In particular embodiments, the device exhibits a mass reduction of about 10 percent or more, e.g. about 50 percent or more, after a period of implantation of one day or more, e.g. about 60 days or more, about 180 days or more, about 600 days or more, or 1000 days or less. In embodiments, the device exhibits fragmentation by erosion processes. The fragmentation occurs as, e.g., some regions of the device erode more rapidly than other regions. The faster eroding regions become weakened by more quickly eroding through the body of the endoprosthesis and fragment from the slower eroding regions. The faster eroding and slower eroding regions may be random or predefined. For example, faster eroding regions may be predefined by treating the regions to enhance chemical reactivity of the regions. Alternatively, regions may be treated to reduce erosion rates, e.g., by using coatings. In embodiments, only portions of the device exhibits erodibilty. For example, an exterior layer or coating may be erodible, while an interior layer or body is non-erodible. In embodiments, the endoprosthesis is formed from an erodible material dispersed within a non-erodible material such that after erosion, the device has increased porosity by erosion of the erodible material.

Erosion rates can be measured with a test device suspended in a stream of Ringer's solution flowing at a rate of 0.2 m/second. During testing, all surfaces of the test device can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter.

Aspects and/or embodiments may have one or more of the following advantages. The growth and/or migration of cells, such as endothelial or red blood cells can be controlled, e.g., the migration of the cells can be oriented radially, longitudinally, or in both directions around and/or along the strut. Such increased growth and migration may facilitate endothelial encapsulation of the endoprosthesis, e.g., stent. The endoprosthesis can also have reduced restenosis and/or thrombogenecity in vivo. The porosity of the endoprosthesis, can be controlled, e.g., increased, thereby controlling the exposure of the endoprosthesis to fluids, e.g., bodily fluids. Enhanced fluid exposure can increase erosion of an erodible (e.g., bioerodible) portion of the endoprosthesis. Increased porosity of the endoprosthesis can also increase the elution rate of a therapeutic agent from the endoprosthesis, e.g., a drug-eluting stent. Increased elution of the therapeutic agent can have the additional advantage of reducing the amount of agent used in the endoprosthesis.

Other aspects, features, and advantages will be apparent from the description and drawings, and from the claims.

DESCRIPTION OF DRAWINGS

FIGS. 1A-1C are longitudinal cross-sectional views, illustrating delivery of a stent in a collapsed state (FIG. 1A), expansion of the stent (FIG. 1B) and deployment of the stent (FIG. 1C).

DETAILED DESCRIPTION

Figure 2A:
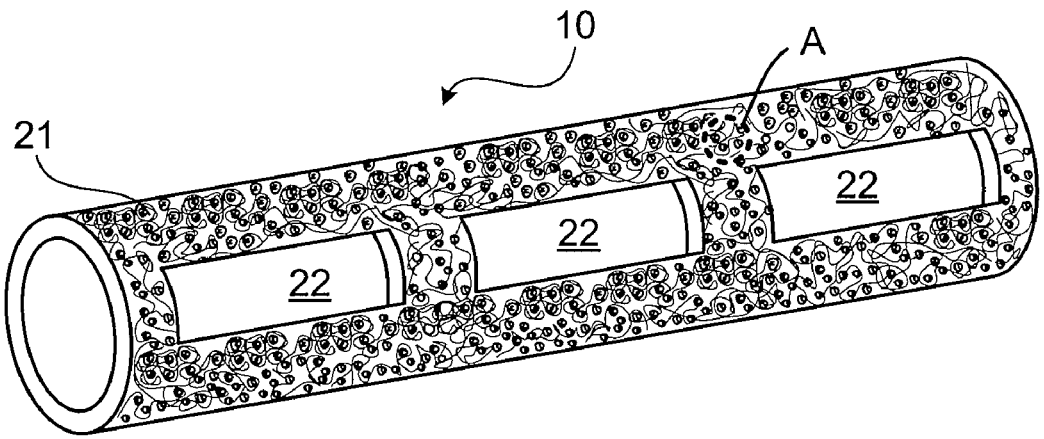
FIG. 2A is a perspective view of a stent.

Referring to FIGS. 1A-1C, in use stent 10 is placed over a balloon 12 carried near the distal end of a catheter 14, and is directed through a lumen 15 (FIG. 1A) until the portion carrying the balloon and stent reaches the region of an occlusion 18. The stent 10 is then radially expanded by inflating the balloon 12 and pressed against the vessel wall with the result that occlusion 18 is compressed, and the vessel wall surrounding it undergoes a radial expansion (FIG. 1B). The pressure is then released from the balloon and the catheter 14 is withdrawn from the vessel (FIG. 1C).

Figure 2B:
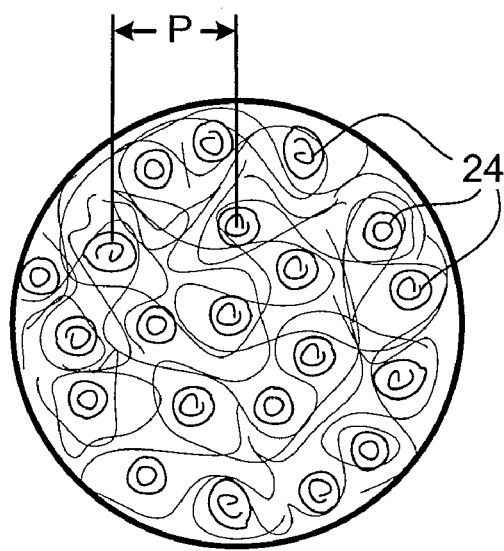
FIG. 2B is an enlarged view of region A in FIG. 2A.
Figure 2C:
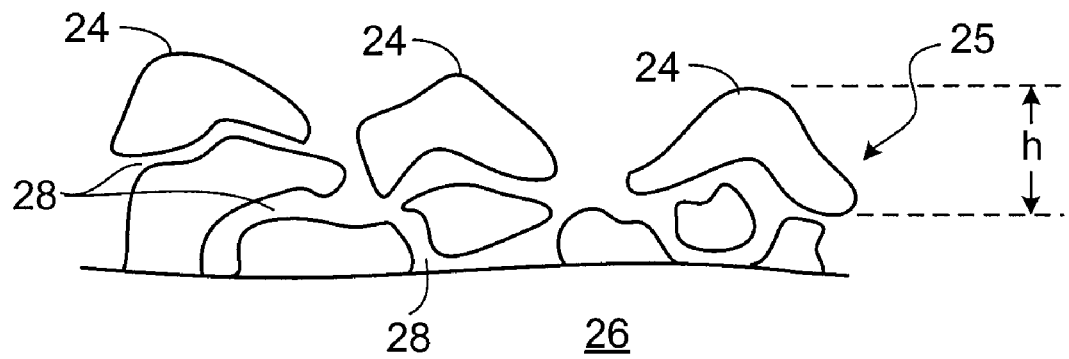
FIG. 2C is a cross-sectional view through the stent wall.
Figure 2D:
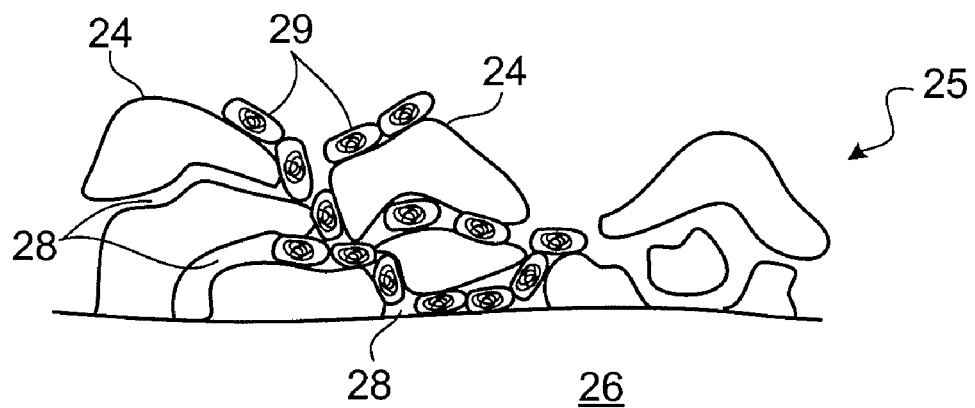
FIG. 2D is a cross-sectional view through the stent wall in FIG. 2C with cells interspersed within the polymer layer.

Referring to FIG. 2A, the stent 10 is a generally tubular device defined by a stent wall 21 including fenestrations 22 separated by struts. Referring to FIG. 2B, an enlarged view of the region A in FIG. 2A, the surface of the stent wall is composed of polymer that has a controlled morphology characterized by bumps or nodules 24 that facilitates endothelization. Referring to FIG. 2C, a cross-section through the stent wall, the nodules 24 are formed in a polymer layer 25 provided on the outside surface of a body 26 of the stent. The layer 25 defines within its thickness a porous structure characterized by tortuous channels 28. Referring to FIG. 2D, a cross-sectional view through the stent wall, cells 29 (e.g., endothelial cells) migrate on the outside surface of the polymer 25 and/or through tortuous channels 28 within the polymer.

Referring particularly to FIG. 2B, in embodiments, the nodules 24 have a substantially uniform periodicity, P, of about 5 microns to about 50 microns, e.g., typically about 15 to 25 microns, e.g., about 20 microns. The nodule diameter, d, is about 5 to 50 microns, e.g., typically about 10 to 30 microns, e.g., about 19 microns or more in diameter (e.g., a radius of 9.5 microns that equals to an area of about 283 square microns). The nodule height, h, is less than 50 microns, e.g., typically less than 25 microns, e.g., about 1 to 10 microns (e.g., about 6 microns). The density of nodules is about 0.0010 to 0.1 nodules per square micron, typically about 0.002 to 0.0050 nodules per square micron, e.g., about 0.0025 nodules per square micron. The morphology defines spaces 28 between the features having a width and depth of about 50 to 2000 nm or more, e.g., about 1000 nm, or about the size of a typical endothelial cell. The thickness of the polymer morphology layer can vary as needed, but is typically in the range of less than 100 microns, typically less than 50 microns; and more typically about 0.5 to 20 microns.

Figure 3A:
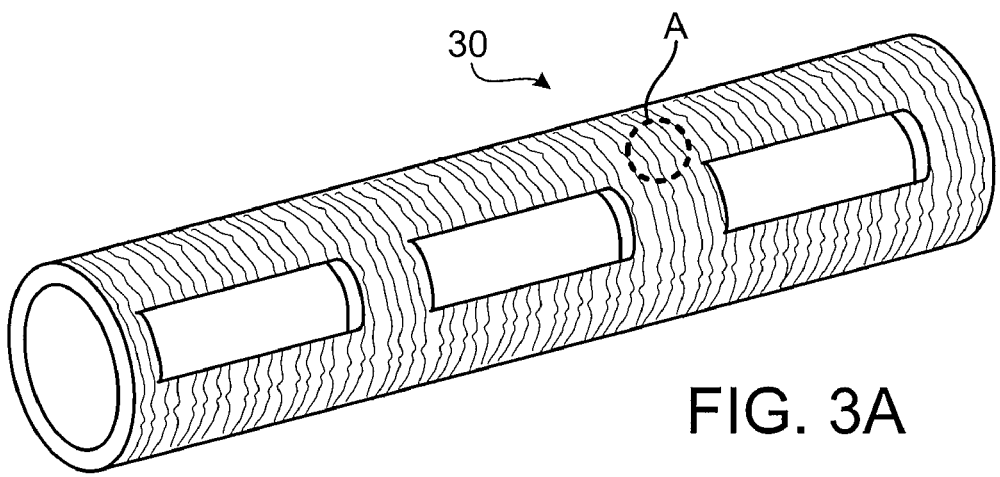
FIG. 3A is a perspective view of a stent.
Figure 3B:
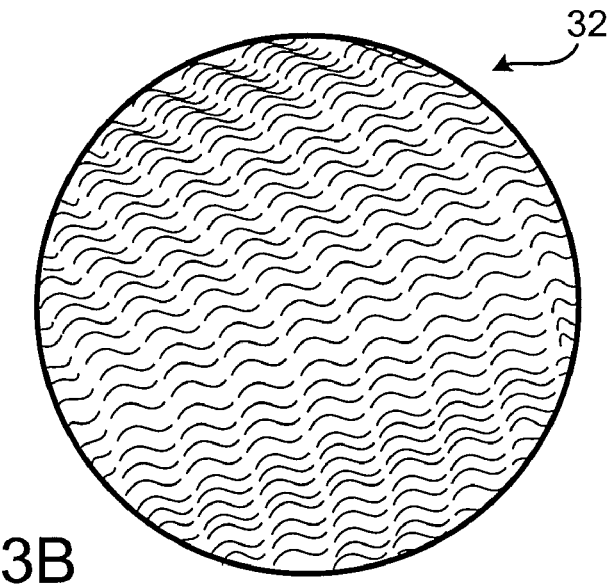
FIG. 3B is an enlarged view of region A in FIG. 3A.
Figure 3C:
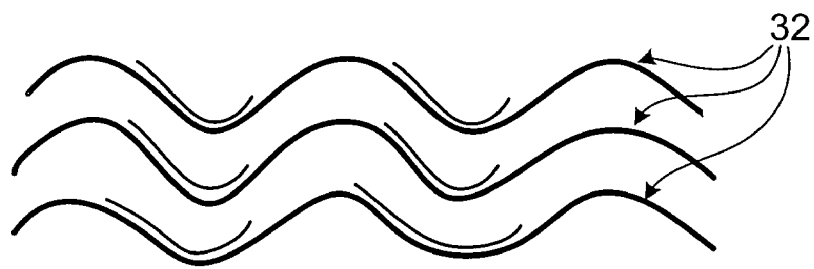
FIG. 3C is an enlarged three-dimensional view of the ribs in FIGS. 3A-3B.

Referring to FIGS. 3A-3C, a stent 30 with a radially ribbed morphology is illustrated. Referring to FIG. 3B, an enlarged view of the region A in FIG. 3A, the surface of the stent wall is composed of ribs 32 that are arranged radially around the stent in generally parallel rows. Referring to FIG. 3C, an enlarged three-dimensional view of the ribs in FIG. 3B, a plurality of ribs 32 having a wave-like morphology is shown. The ribs can have a wave-like morphology as shown in FIG. 3C, or have a more linear configuration. In embodiments, the ribs provide a surface to facilitate the migration of cells, e.g., endothelial cells. Typically, the radial ribs are about 100 to 5000 nm, about 500 to 2500 nm, more typically about 800 to 1500 nm in depth, and have a periodicity of less than 50 µm, typically less than 20 µm, more typically less than 13 µm. In one exemplary embodiment, a plurality of ribs extends radially around the strut, e.g., overlaying the stent wall. The ribs can extend radially in any desired configuration, e.g., a spiral configuration.

The size, period and pattern of the morphology, as well as the porosity can be controlled to facilitate the growth and/or migration of endothelial cells, and/or the delivery of a therapeutic agent from the cavity. In some embodiments, the morphology provides a tortuous interstitial path that facilitates cell, e.g., endothelial cell, in-growth and migration (e.g., randomly disposed within a porous surface). In embodiments, cell migration can be guided, e.g., proceeding radially, longitudinally, or both, along the surface of the stent. The width and depth of the morphology, as well as the porosity can be adapted to provide different topographical cues to the cells, thus influencing their migration. In some embodiments, the morphology includes one or more agents that stimulate endothelial cell growth and/or attachment (e.g., placental growth factors, such as PlGF-1 and PlGF-2, and vascular endothelial growth factor (VEGF)).

Increasing the porosity of the stent can increase its exposure to fluids, e.g., bodily fluids, thus, increasing the rate of drug elution from a drug-eluting stent, or increasing erosion rate of an erodible stent (e.g., a bioerodible stent). An erodible stent may contain a therapeutic agent, the release of which can be further increased as the stent erodes. In one embodiment, a plurality of nodules formed in an outer layer of the stent can be used as wells for immediate release of a therapeutic agent, e.g., heparin. In other embodiments, the therapeutic agent can be embedded within the morphology layer or one or more layers located beneath or over the morphology layer. The release of the therapeutic agent will depend on factors, such as the solubility of the therapeutic agent being released and the porosity of the outer layer of the stent.

Figure 4:
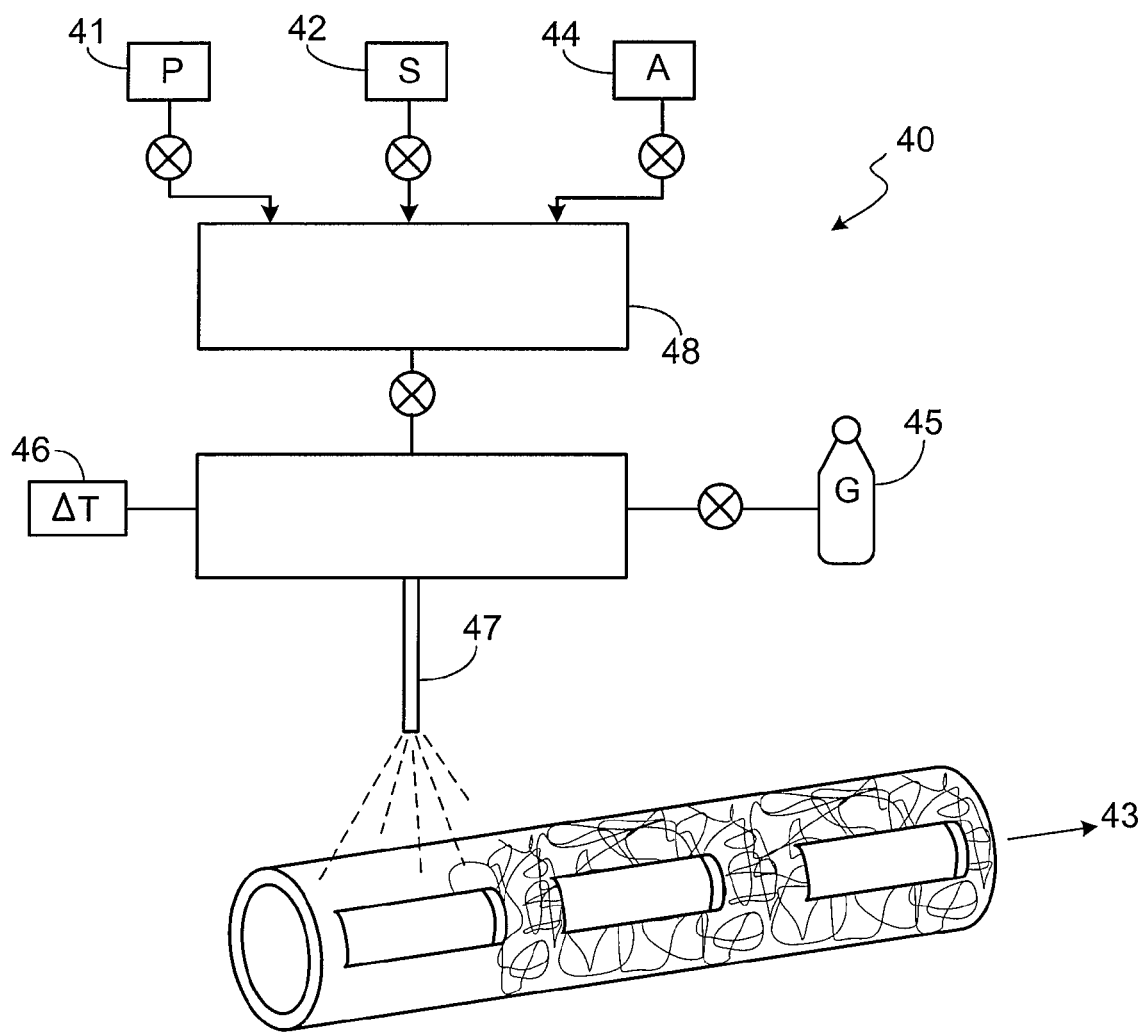
FIG. 4 is a schematic of a system for applying a controllable morphology to the stent.

Referring to FIG. 4, the morphology can be controlled by altering the parameters of a spray system 40 used to form the morphology layer. The system 40 includes a nozzle 47 which sprays a solution onto a stent 43. The nozzle pressurizes the solution with gas from a supply 45. The temperature of the solution is controlled using a temperature controller 46. The solution is held in a reservoir 48 and can include selected aliquots of polymer material 41, solvent 42, and additive 44.

In particular, the morphology can be controlled by modifying the droplet speed and size, the evaporation rate or volatility of the solution and/or the surface energy of the solvent. Larger droplets and slower drop velocity increase the size of morphological features such as nodules. A more rapid evaporation rate increases the nodular nature of the morphology, and reduces the size and periodicity of the nodules. A higher surface energy, relative to the surface energy of the stent surface, promotes nodular formation by promoting a beading of the solution on the stent surface. The evaporation rate or volatility and the surface energy can be controlled by the selection of the solvent and/or use of additives.

In particular embodiments, the drop velocity is about 5-35 meter/second. For example, to increase the droplet size, the velocity of the sprayed formulation can be decreased to about 10-15 meter/second. The spraying distance can also be adjusted depending on the volatility of the formulation. The evaporation rate and/or volatility of the solvent can be controlled by controlling the temperature of the spray solution, the stent and/or the composition of the solution.

In particular embodiments, the formulation (also referred to herein as "solution") includes a blend of solvents of different boiling points. For example, the blend can include solvents with a boiling point in the range of about 50 to about 180° C. In particular embodiments, the solvent is a blend of higher boiling point solvents, with boiling points in the range of 100 to 150° C., and lower boiling point solvents such as boiling point in the range of 50 to 90° C. In one embodiment, the higher boiling point solvent is present in an amount of about 40% or more, e.g., about 50-90%. In embodiments, the porosity can be increased, for example, by coating the stent with a formulation that includes a higher proportion of a solvent having a lower boiling point and/or higher volatility. For example, the formulation can include a solvent with a boiling point in the range of 50 to 90° C., typically 55 to 85° C. (e.g., tetrahydrofluran (THF), acetone 56° C., isopropyl alcohol 82.2° C., and methanol 64.5° C.) mixed with a solvent having a higher boiling point in the range of 110 to 140° C. (e.g., toluene or xylene). The proportion of the more volatile solvent (e.g., THF) in the formulation can be 20%, 30%, 40%, and more typically, 50%, 60%, 70%, 80%, 90%, 95%, 98%, 99% relative to the less volatile solvent (e.g., toluene or xylene). Additional solvents having similar volatile properties as THF, toluene or xylene can be used instead of, or in addition to, the solvents described herein. The less volatile solvent, e.g., toluene, may, optionally, increase the wettability of the formulation.

The surface energy of the stent material or solution can be selected to cause the solution to bead on the stent surface. In embodiments, the surface energy of the solution is lower than the surface energy of the stent surface onto which the solution is applied. In embodiments, the surface energy of the stent material is about 26 to 34 mJ/m$^2$, e.g., about 30 mJ/m$^2$. The formulation can optionally, include one or more other components, including a polymer, a surfactant, and/or a therapeutic agent, as described below. The solvent typically solubilizes about 0.05 to 30% (by weight), e.g., about 0.1 to 1% polymer. Suitable polymers include styrene-isobutylene-styrene (SIBs), polyether block amide (PEBA, PEBAX®), nylon, and polyurethanes. Polymers suitable for incorporation of a therapeutic agent are described in Schwarz et al. U.S. Pat. No. 6,368,658. The solution can include the polymer or a pre-polymer (e.g. monomers), which are polymerized on the stent.

The ribbed morphology can be formed using a formulation that includes one or more surfactants as an additive. Suitable surfactants include polymeric dispersants, such as polymeric fatty acids, including polymeric dispersants having a polyakoxylate head group and a polyester tail group, e.g., Zephrym; polymeric dispersants having a fatty acid head group and a polyester tail group, e.g., Hypermer KD-3 and Hypermer KD-4; as well as polymeric dispersants having a polyamine head group and a polyester tail group, e.g., Atlox LP6 (manufactured by Uniqema, Imperial Chemical Industries). In embodiments, the surfactant (e.g., one or more of Zephrym, Hypermer KD-3, Hypermer KD-4 and Atlox LP6) is at least 10%, 15%, 20%, 25% or 30% of the formulation coating. Without being bound by theory, the surfactant is believed to form micelles about the polymer material, which inhibits polymer agglomeration. As the solvent dries, the coating contracts to form grooves. The transition between the ribbed structure and a nodular pocketed morphology structure can be controlled by controlling the amount of high boiling point additive relative to the surfactant. The ribs need not cover the entire radial surface of the stent, e.g., ribs can extend only on the outer diameter, the inner diameter, or a side wall, or portion thereof.

Figure 5A:
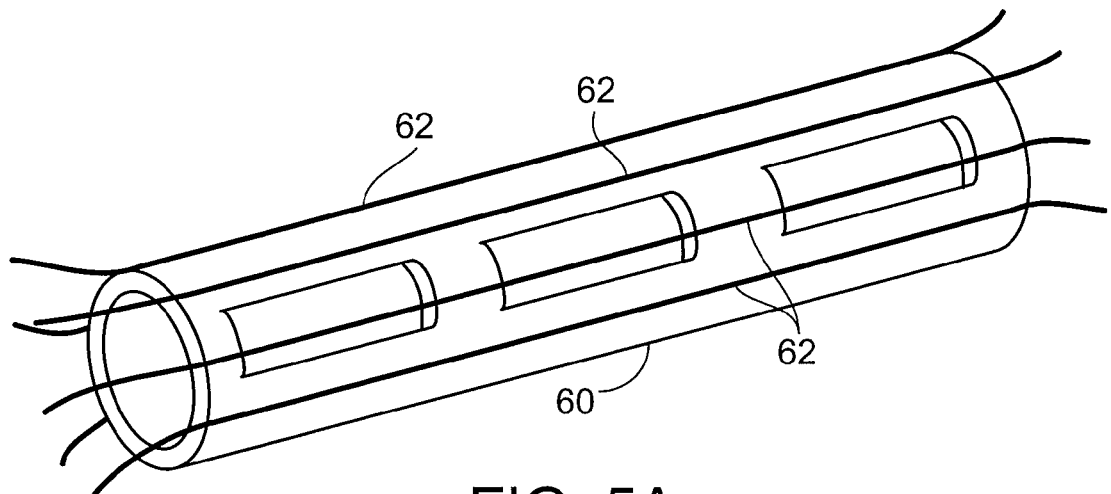
FIG. 5A is a perspective schematic of a stent including a mask.
Figure 5B:
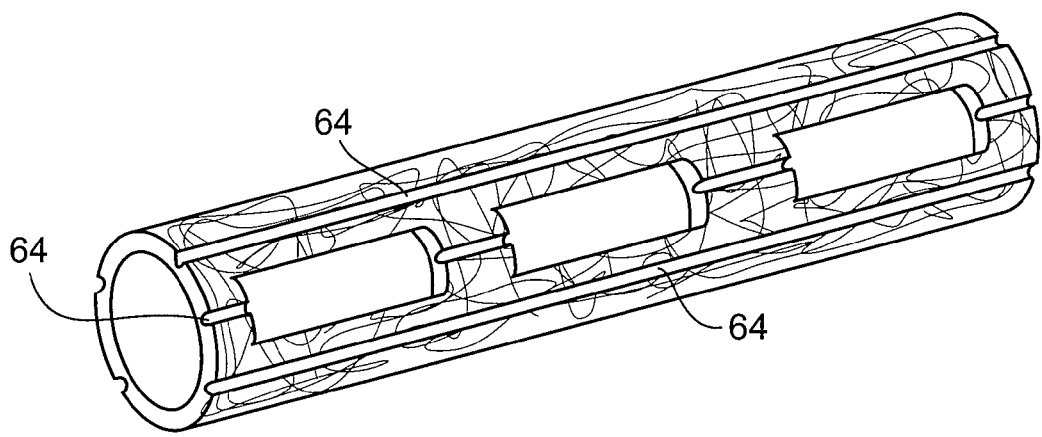
FIG. 5B is a perspective schematic of the stent in 5A after application of a morphology to the stent and removal of the mask.
Figure 6:
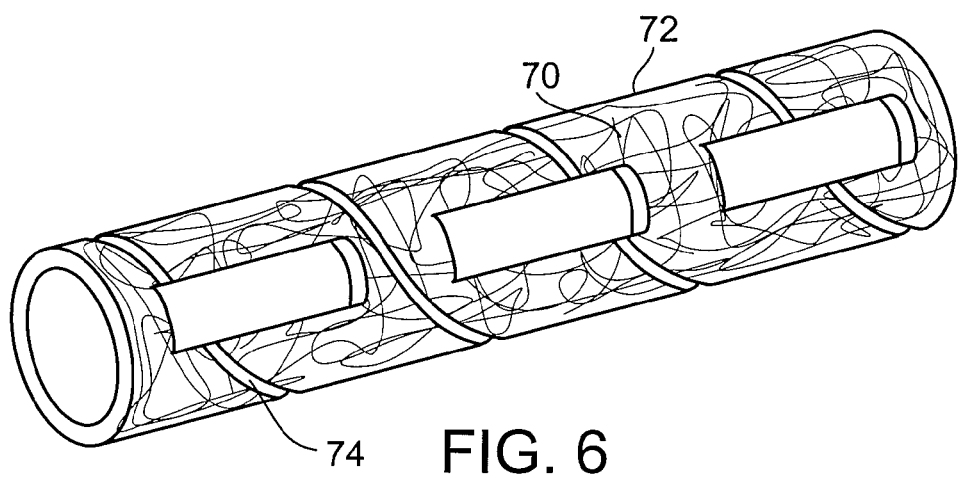
FIG. 6 is a perspective view of a stent.

Referring as well to FIGS. 5A and 5B, in embodiments, the stent 60 can be provided with a mask 62 so that the solution is applied in a desired pattern. In the embodiment of FIG. 5A, the mask is provided in the form of a plurality of wires longitudinally arranged onto the stent; when the wires are removed after spraying, the polymer layer is interrupted by a series of axial grooves 64 that encourage endothelial growth along the length of the stent. Referring to FIG. 6, a stent 70 illustrated includes a surface morphology 72 interrupted by a spiral groove or gap 72. The spiral groove 74 is formed utilizing a wire mask wrapped around the stent during application of the morphology layer. One or more longitudinal grooves can be alternatively created by laser ablation and/or mechanical means (e.g., using blades or by expanding a cutting balloon inside the stent). Typically, the longitudinal grooves are about 100 to 5000 nm, about 500 to 2500 nm, more typically about 800 to 1500 nm in depth; have a periodicity of less than 50 microns, typically less than 20 microns, more typically less than 13 microns, and have a length of about 50 microns to 3 mm, typically about 75 microns to 500 microns, more typically about 100 microns. The grooves can extend to the entire surface of the stent (e.g., an outer or inner surface), or a portion of the coating (e.g., 25%, 50%, or 75% of the length of the stent).

In embodiments, any of the morphologies described above can be applied over the entire stent or over only portions of the stent (e.g. over the inner or outer portions). Different morphologies can be provided in different portions (e.g., the inner and the outer surface). The morphology can be applied by incorporating the polymer in the solution which is applied to the stent to form a coating, or the solvent can be applied to a stent already including a polymer. The coating can be applied to a previously applied coating, e.g., a drug-eluting coating, to provide a multilayer system including an inner drug-eluting coating and an outer morphology coating. The drug-eluting coating can also be applied over a previously applied morphology coating. The stent body itself can be formed of a polymer, which is processed to form a particular morphology and/or include a drug. The solution can be applied by techniques other than spraying, e.g., by dipping the stent into the solution. The components of the solution can be applied sequentially to the stent surface, rather than simultaneously.

The stent body can be formed of metal, polymer or ceramic that is bioerodible or biostable. The morphology layer can be a contiguous outer portion of a polymer stent body. Suitable bioerodible materials include one or more of a metallic component (e.g., a metal or alloy), a non-metallic component (e.g., a biodegradable polymer), or any combination thereof. Bioerodible materials are described, for example, in U.S. Pat. No. 6,287,332 to Bolz; U.S. Patent Application Publication No. US 2002/0004060 A1 to Heublein; U.S. Pat. Nos. 5,587,507 and 6,475,477 to Kohn et al. Examples of bioerodible metals include alkali metals, alkaline earth metals (e.g., magnesium), iron, zinc, and aluminum. Examples of bioerodible metal alloys include alkali metal alloys, alkaline earth metal alloys (e.g., magnesium alloys), iron alloys (e.g., alloys including iron and up to seven percent carbon), zinc alloys, and aluminum alloys. Examples of bioerodible non-metals include bioerodible polymers, such as, e.g., polyanhydrides, polyorthoesters, polylactides, polyglycolides, polysiloxanes, cellulose derivatives and blends or copolymers of any of these. Bioerodible polymers are disclosed in U.S. Published Patent Application No. 2005/0010275, filed Oct. 10, 2003; U.S. Published Patent Application No. 2005/0216074, filed Oct. 5, 2004; and U.S. Pat. No. 6,720,402, the entire contents of each of which is hereby incorporated by reference herein.

Other examples of bioerodible materials include polyelectrolytes. Polyelectrolytes are polymers having charged (e.g., ionically dissociable) groups. The number of these groups in the polyelectrolytes can be so large that the polymers are soluble in polar solvents (including water) when in ionically dissociated form (also called polyions). Depending on the type of dissociable groups, polyelectrolytes can be classified as polyacids and polybases. When dissociated, polyacids form polyanions, with protons being split off. Polyacids include inorganic, organic and biopolymers. Examples of polyelectrolytes and methods of forming polyelectrolyte-containing stents are described in WO 2005/115496 and commonly assigned U.S. Ser. No. 10/985,242 entitled "Medical Devices and Methods of Making the Same" by Atanasoska. L. et al. filed on Nov. 10, 2004, the contents of both of which are incorporated by reference. Examples of polyacids include polyphosphoric acids, polyvinylsulfuric acids, polyvinylsulfonic acids, polyvinylphosphonic acids and polyacrylic acids. Examples of the corresponding salts, which are called polysalts, include polyphosphates, polyvinylsulfates, polyvinylsulfonates, polyvinylphosphonates and polyacrylates. Polybases contain groups that are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations. Some polyelectrolytes have both anionic and cationic groups, but nonetheless have a net positive or negative charge.

The polyelectrolytes can include those based on biopolymers. Examples include alginic acid, gum arabicum, nucleic acids, pectins and proteins, chemically modified biopolymers such as carboxymethyl cellulose and lignin sulfonates, and synthetic polymers such as polymethacrylic acid, polyvinylsulfonic acid, polyvinylphosphonic acid and polyethylenimine. Linear or branched polyelectrolytes can be used. Using branched polyelectrolytes can lead to less compact polyelectrolyte multilayers having a higher degree of wall porosity. In some embodiments, polyelectrolyte molecules can be crosslinked within or/and between the individual layers, to enhance stability, e.g., by crosslinking amino groups with aldehydes. Furthermore, amphiphilic polyelectrolytes, e.g., amphiphilic block or random copolymers having partial polyelectrolyte character, can be used in some embodiments to affect permeability towards polar small molecules. Other examples of polyelectrolytes include low-molecular weight polyelectrolytes (e.g., polyelectrolytes having molecular weights of a few hundred Daltons up to macromolecular polyelectrolytes (e.g., polyelectrolytes of synthetic or biological origin, which commonly have molecular weights of several million Daltons). Still other examples of polyelectrolyte cations (polycations) include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations. Examples of polyelectrolyte anions (polyanions) include poly(styrenesulfonate) polyanions (e.g., poly(sodium styrene sulfonate) (PSS)), polyacrylic acid polyanions, sodium alginate polyanions, Eudragit polyanions, gelatin polyanions, hyaluronic acid polyanions, carrageenan polyanions, chondroitin sulfate polyanions, and carboxymethylcellulose polyanions.

In other embodiments, the stent can include one or more nonerodible or biostable materials in addition to one or more bioerodible materials. For example, the bioerodible material may be provided as a coating in a biostable stent body.

Examples of biostable materials include stainless steel, tantalum, nickel-chrome, cobalt-chromium alloys such as Elgiloy® and Phynox®, Nitinol (e.g., 55% nickel, 45% titanium), and other alloys based on titanium, including nickel titanium alloys, thermo-memory alloy materials. Stents including biostable and bioerodible regions are described, for example, in U.S. patent application Ser. No. 11/004,009, filed on Dec. 3, 2004, and entitled "Medical Devices and Methods of Making the Same." The material can be suitable for use in, for example, a balloon-expandable stent, a self-expandable stent, or a combination of both (see e.g., U.S. Pat. No. 5,366,504).

The stent can be manufactured, or the starting stent can be obtained commercially. Methods of making stents are described, for example, in U.S. Pat. No. 5,780,807 and U.S. Application Publication US-2004-0000046-A1. Stents are also available, for example, from Boston Scientific Corporation, Natick, Mass., USA, and Maple Grove, Minn., USA. The stent can be formed of any biocompatible material, e.g., a metal or an alloy, as described herein. The biocompatible material can be suitable for use in a self-expandable stent, a balloon-expandable stent, or both. Examples of other materials that can be used for a balloon-expandable stent include noble metals, radiopaque materials, stainless steel, and alloys including stainless steel and one or more radiopaque materials.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total. Suitable therapeutic agents are described in U.S. Published Application No. 2005/0216074, entitled "Implantable Medical Devices" by Sahatjian, R. et al., the contents of which are incorporated by reference.

Medical devices, in particular endoprostheses, as described above include implantable or insertable medical devices, including catheters (for example, urinary catheters or vascular catheters such as balloon catheters), guide wires, balloons, filters (e.g., vena cava filters), stents of any desired shape and size (including coronary vascular stents, aortic stents, cerebral stents, urology stents such as urethral stents and ureteral stents, biliary stents, tracheal stents, gastrointestinal stents, peripheral vascular stents, neurology stents and esophageal stents), grafts such as stent grafts and vascular grafts, cerebral aneurysm filler coils (including GDC-Guglilmi detachable coils-and metal coils), filters, myocardial plugs, patches, pacemakers and pacemaker leads, heart valves, and biopsy devices. In one embodiment, the medical device includes a catheter having an expandable member, e.g., an inflatable balloon, at its distal end, and a stent or other endoprosthesis (e.g., an endoprosthesis or stent as described herein). The stent is typically an apertured tubular member (e.g., a substantially cylindrical uniform structure or a mesh) that can be assembled about the balloon. The stent typically has an initial diameter for delivery into the body that can be expanded to a larger diameter by inflating the balloon. The medical devices may further include drug delivery medical devices for systemic treatment, or for treatment of any mammalian tissue or organ.

The medical device, e.g., endoprosthesis, can be generally tubular in shape and can be a part of a stent. Simple tubular structures having a single tube, or with complex structures, such as branched tubular structures, can be used. Depending on specific application, stents can have a diameter of between, for example, 1 mm and 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stents can also be preferably bioerodible, such as a bioerodible abdominal aortic aneurysm (AAA) stent, or a bioerodible vessel graft.

In some embodiments, the medical device, e.g., endoprosthesis, is used to temporarily treat a subject without permanently remaining in the body of the subject. For example, in some embodiments, the medical device can be used for a certain period of time (e.g., to support a lumen of a subject), and then can disintegrate after that period of time. Subjects can be mammalian subjects, such as human subjects (e.g., an adult or a child). Non-limiting examples of tissues and organs for treatment include the heart, coronary or peripheral vascular system, lungs, trachea, esophagus, brain, liver, kidney, bladder, urethra and ureters, eye, intestines, stomach, colon, pancreas, ovary, prostate, gastrointestinal tract, biliary tract, urinary tract, skeletal muscle, smooth muscle, breast, cartilage, and bone.

EXAMPLES

Stents are spray-coated with SIBs using a concentric nozzle-type gas pressurized nebulizer. The nozzle is pressurized with $N_2$ gas at about 5 psi. The flow of solvent solution is about 20 ml/hr per hour (although solvent flow rates in the range of 10 to 40 ml/hr can be used). The flow rate of the gas in the nozzle is about 15 liter/min (although gas flow rates ranging from 5 to 20 liter/min can be used). The diameter of the nozzle orifice is about 1 mm. Suitable nozzle designs are commercially available as the Microcoat 800 series through EFD Inc., a Nordson Company (East Providence, R.I. USA). The solution and stent temperature for spray-coating is about 20° C. The spraying distance is about 50 mm. Magnified images of the stent are obtained by scanning electron microscopy (SEM) and optical microscopy as indicated below.

Figure 7:
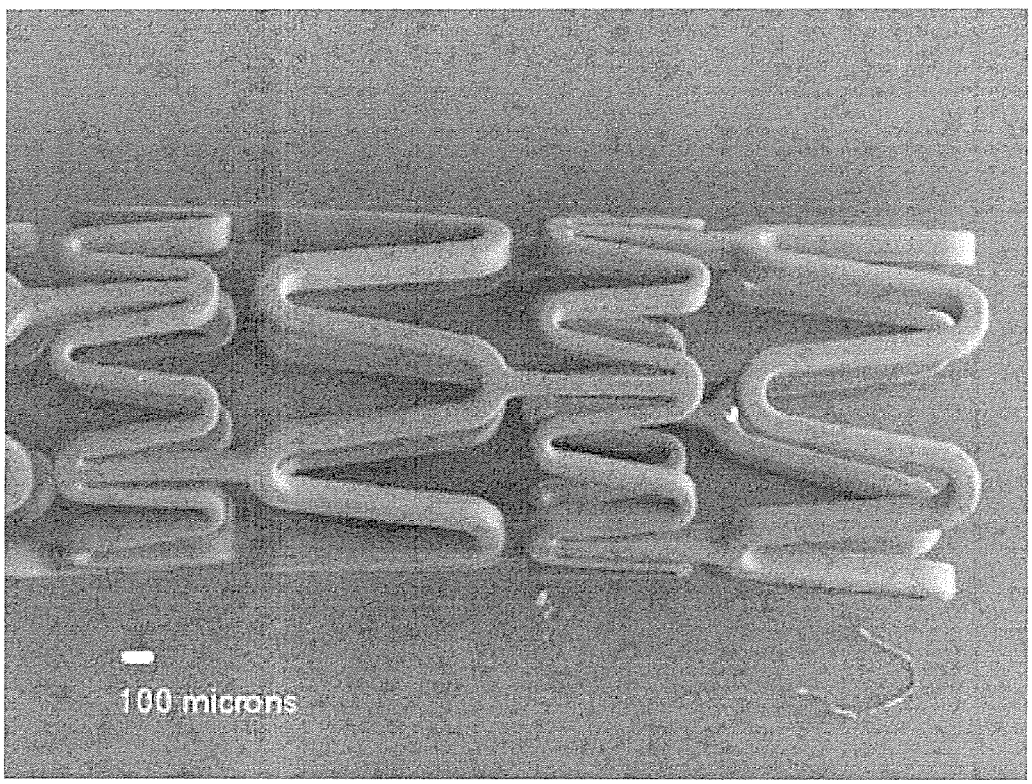
FIGS. 7-13 are photographs of stents.
Like reference symbols in the various drawings indicate like elements.

Referring to FIG. 7, which shows a SEM image of a stainless steel body after spraying with a solution consisting of about 94% toluene, about 5% THF and a polymer (SIBs). SIBs is present at about 1% (by weight). The coating exhibits a smooth morphology as shown in FIG. 7 (scale bar corresponds to about 100 microns).

Referring to the Table, to form outer layers of various porosities and morphologies, a coating solution is used that includes toluene and varying amounts of low boiling point solvent THF, with varying amounts of surfactant Zephrym (manufactured by Uniqema), with or without a drug (paclitaxel).

TABLE

| Solvent | Low Boiling Pt. Solvent | Surfactant | Drug | Morphology | Photo |
|---|---|---|---|---|---|
| Toluene | 99% THF | y (0.3%) | Y | Nodules | FIG. 8, 9 |
| Toluene | 99% THF | y (0.3%) | N | Nodules | FIG. 10 |
| Toluene | 5% THF | y (30%) | N | Ribs | FIG. 11 |
| Toluene | ~50% THF | y (30%) | N | Broken ribs | FIG. 12 |
| Toluene | ~90% THF | y (10%) | N | Broken ribs | FIG. 13 |

Figure 8:
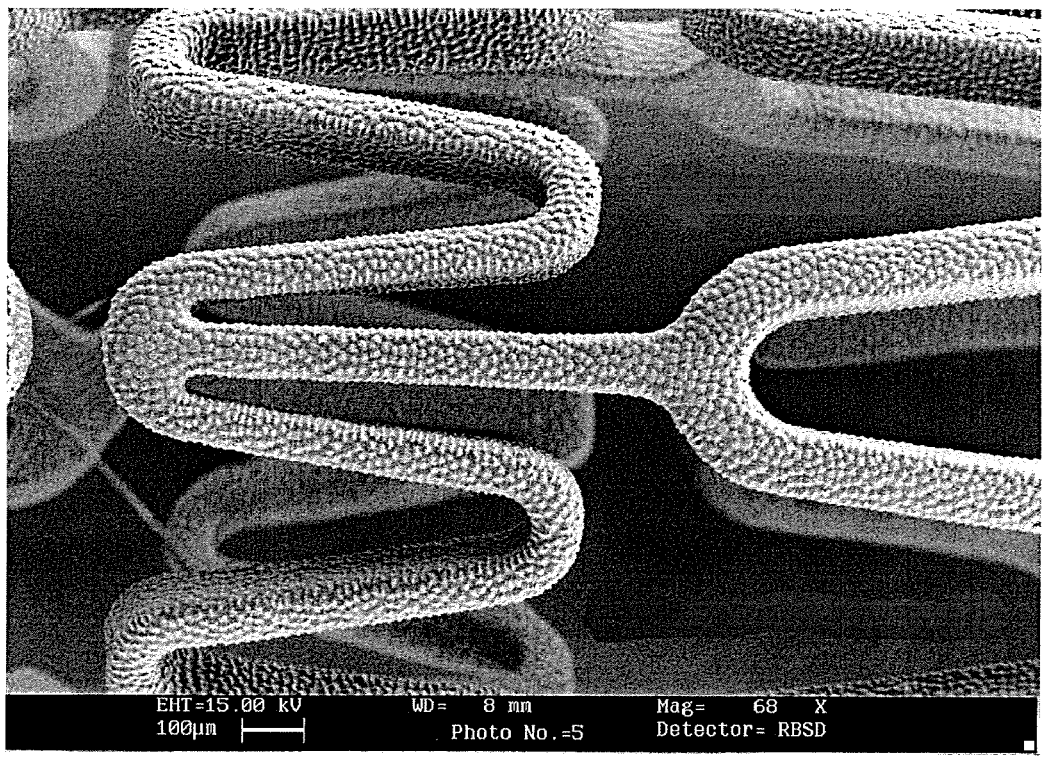
Figure 9:
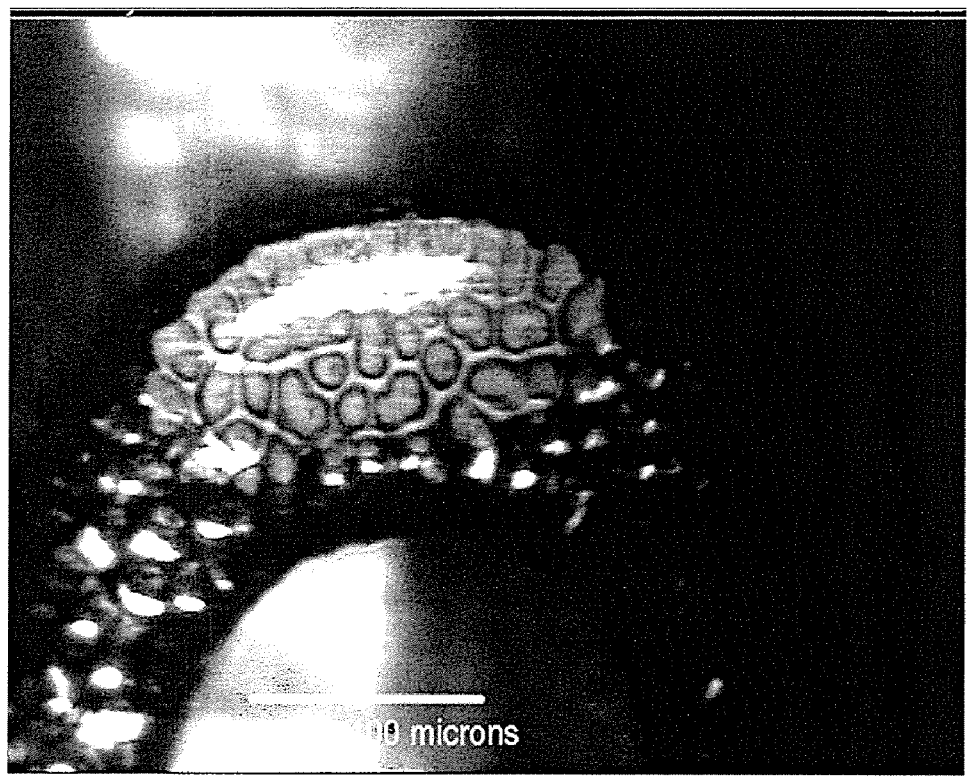
Figure 10:
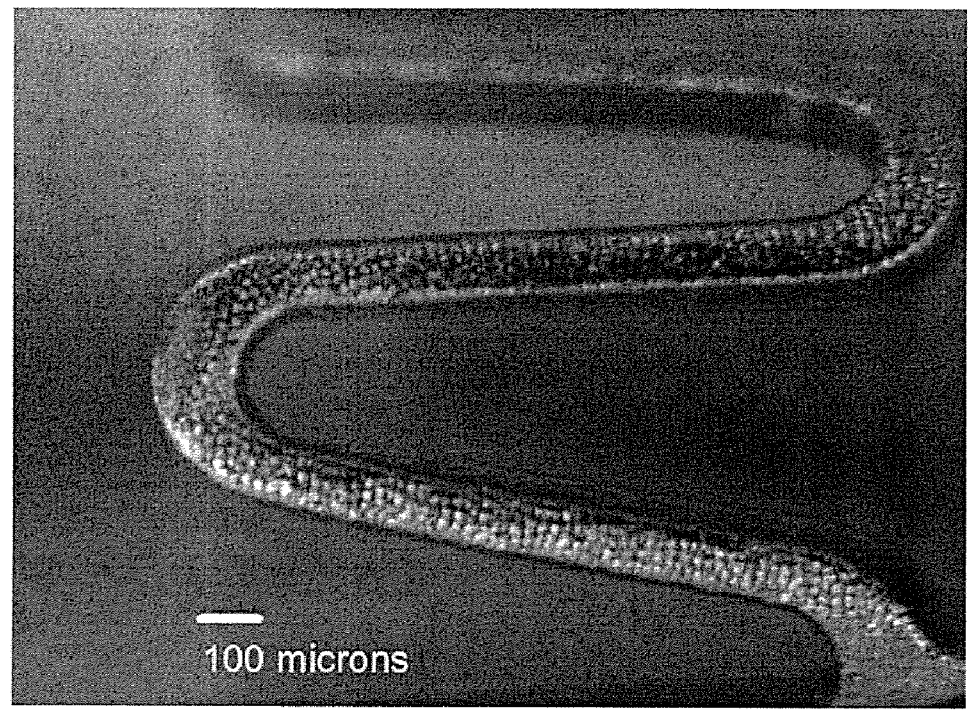

Referring to FIG. 8, a stent having a porous surface resembling small spheres packed together is made by increasing the proportion of THF in the solvent sprayed onto the stainless steel body (magnification is about 68×SEM picture; a scale bar corresponding to about 100 μm is shown in FIG. 8). The formulation sprayed contained 99% THF, 0.05% paclitaxel and a low amount of Zephrym (0.3%). A cross-section through the coating shown in FIG. 8 exposing the porous structure is shown in FIG. 9 (optical microscope image; scale bar corresponds to about 100 microns). Referring to FIG. 10, an optical microscope image shows a similar porous structure as in FIG. 8 formed after applying the THF formulation in the absence of paclitaxel. The scale bar shown in FIG. 10 corresponds to about 100 microns.

Figure 11:
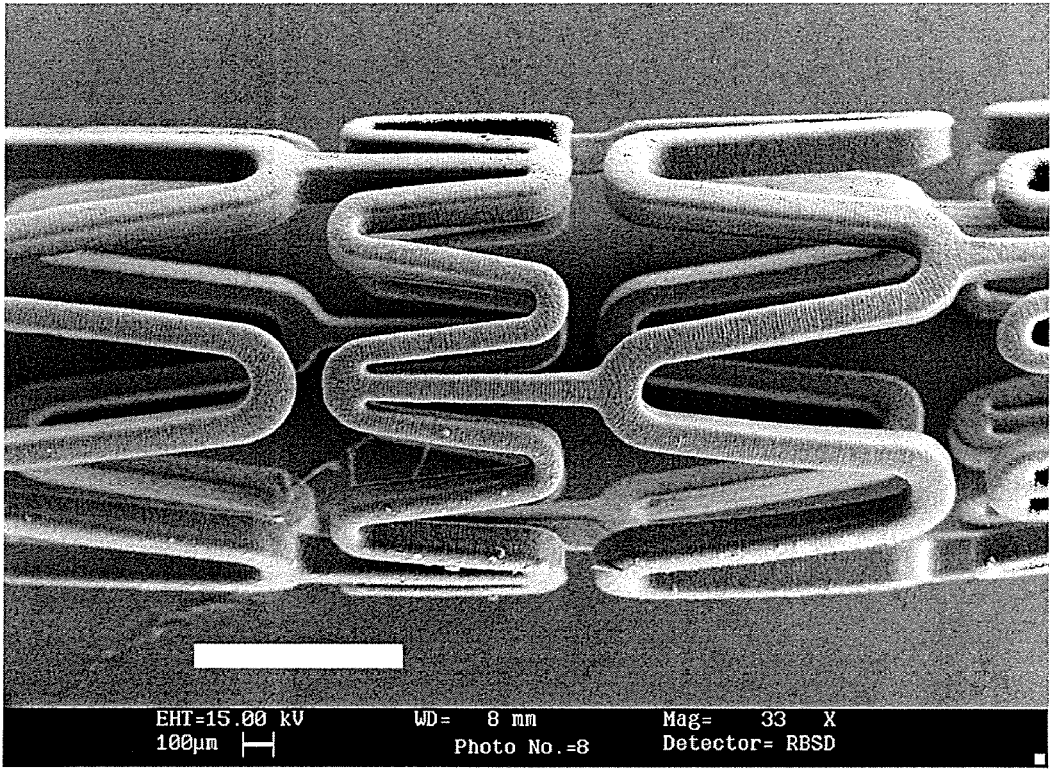

Referring to FIG. 11, a radially ribbed morphology is formed by increasing the concentration of surfactant to about 30% Zephrym in toluene and 5% THF in the coating formulation (magnification is about 33×SEM picture; a scale bar corresponding to about 100 μm is shown in FIG. 11). A stent surface that includes numerous grooves of about 1.5 microns (depth) with a periodicity of about 12.5 microns extending in a radial direction is formed.

Figure 12:
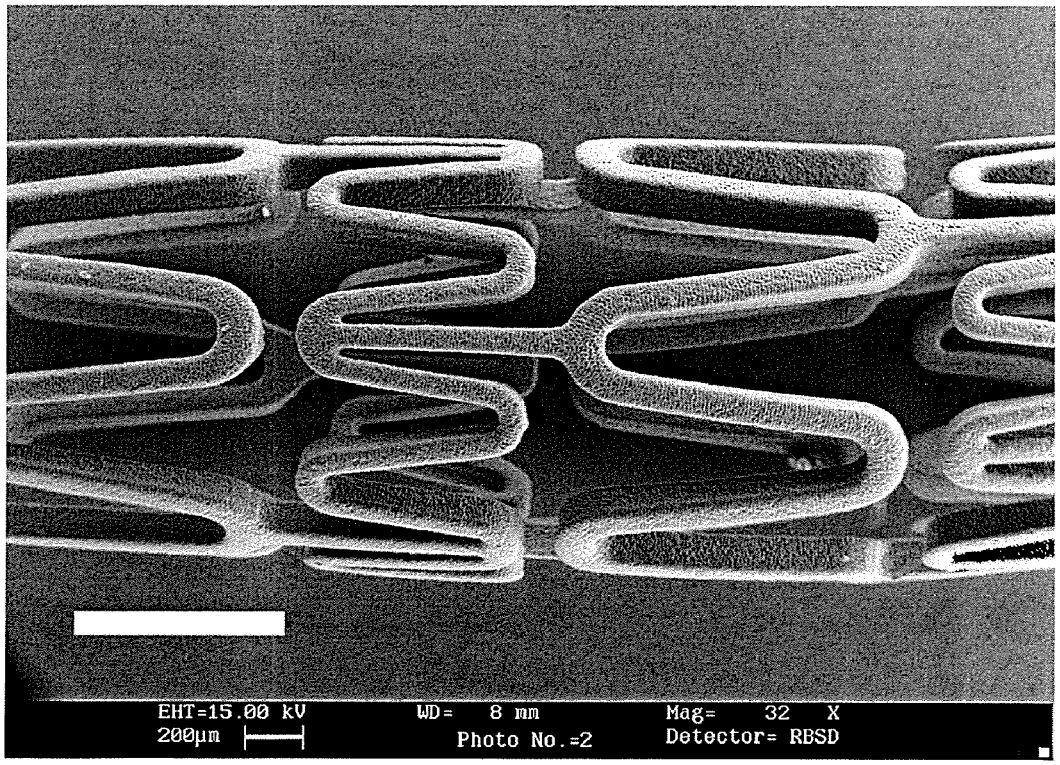
Figure 13:
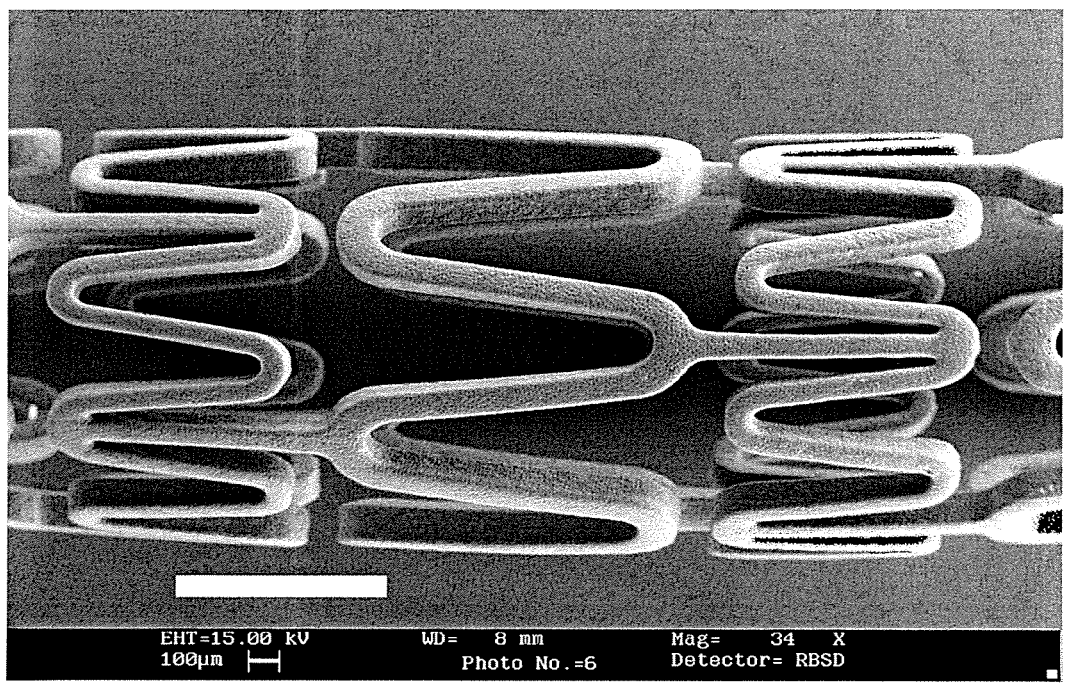

Porous, rib-like morphologies are formed by increasing the concentration of the surfactant and THF in the coating formulation (FIGS. 12-13). Referring to FIG. 12, increasing the concentration of Zephrym to about 30%, and THF to about 50%, in toluene forms the porous ribbed stent surface shown, which has a porosity of about 0.0035 pores per square micron, and further includes numerous grooves extending in a radial direction of about 2 microns (depth) with a periodicity of about 11.5 microns (magnification is about 32×SEM; a scale bar corresponding to about 200 μm is shown in FIG. 12). Referring to FIG. 13, a higher degree of porosity, while preserving the radially ribbed morphology, is obtained by increasing the THF concentration in the coating formulation to greater than 90% in about 10% Zephrym (magnification is about 34×SEM; a scale bar corresponding to about 100 μm is shown in FIG. 13). A stent surface with a high degree of porosity (about 0.0035 pores per square micron) that further includes numerous grooves of about 1 micron (depth) with a periodicity of about 12 microns extending in a radial direction is shown in FIG. 13.

All publications, patent applications, patents, and other references mentioned herein are incorporated by reference herein in their entirety.

Other embodiments are within the scope of the following claims.

What is claimed is:

1. A stent having a surface or portion thereof comprising a polymer having a morphology of surface nodules having a substantially uniform periodicity of about 1 to 50 microns with spaces between the nodules having a width and depth of about 50 to 2000 nanometers, wherein the surface nodules project out of the surface and the spaces between the nodules do not include the polymer.

2. The stent of claim 1, wherein the nodules have a diameter of about 5 to 50 microns.

3. The stent of claim 1, wherein the nodules have a height of about 1 to 10 microns.

4. The stent of claim 1, wherein the nodules are in substantially parallel rows.

5. The stent of claim 4, wherein rows are arranged radially.

6. The stent of claim 1, wherein the polymer is porous.

7. The stent of claim 1, wherein the polymer includes a therapeutic agent.

8. The stent of claim 1, wherein the polymer is bioerodible.

9. The stent of claim 1, wherein the polymer is a layer on a stent body.

10. The stent of claim 9, wherein the stent body comprises a polymer body.

11. The stent of claim 10, wherein the morphology is formed by the same polymer as the polymer body.

12. The stent of claim 9, wherein the stent body comprises a metal.

13. The stent of claim 1, wherein the nodules have a periodicity of about 5 to 50 microns.

14. The stent of claim 1, wherein the surface nodules have a nodule diameter of about 5 to 50 microns.

* * * * *